(12) United States Patent
Larsen et al.

(10) Patent No.: US 12,364,805 B2
(45) Date of Patent: Jul. 22, 2025

(54) SYSTEM FOR SAFE RADIOISOTOPE PREPARATION AND INJECTION

(71) Applicant: MedTrace Pharma A/S, Kongens Lyngby (DK)

(72) Inventors: Peter Larsen, Vaerlose (DK); Martin Stenfeldt, Vedaek (DK); Rune Wiik Kristensen, Hinnerup (DK)

(73) Assignee: MEDTRACE PHARMA A/S, Horsholm (DK)

( * ) Notice: Subject to any disclaimer, the term of this patent is extended or adjusted under 35 U.S.C. 154(b) by 94 days.

(21) Appl. No.: 17/324,257

(22) Filed: May 19, 2021

(65) Prior Publication Data

US 2021/0338921 A1 Nov. 4, 2021

Related U.S. Application Data

(62) Division of application No. 15/738,032, filed as application No. PCT/EP2016/064221 on Jun. 20, 2016.

(30) Foreign Application Priority Data

Jun. 19, 2015 (DK) ................................ 15172904.3

(51) Int. Cl.
*A61M 5/00* (2006.01)
*A61B 6/03* (2006.01)
(Continued)

(52) U.S. Cl.
CPC .......... *A61M 5/007* (2013.01); *A61B 6/4258* (2013.01); *A61M 5/00* (2013.01); *A61M 5/14* (2013.01); *A61M 5/1407* (2013.01); *A61M 5/36* (2013.01); *A61M 5/365* (2013.01); *A61M 39/22* (2013.01); *A61M 39/223* (2013.01);
(Continued)

(58) Field of Classification Search
None
See application file for complete search history.

(56) References Cited

U.S. PATENT DOCUMENTS 3,957,082 A 5/1976 Fuson et al.
4,950,230 A 8/1990 Kendell
(Continued)

FOREIGN PATENT DOCUMENTS

CN 1984690 A 6/2007
DE 2400983 A1 7/1974
(Continued)

OTHER PUBLICATIONS

International Search Report and Written Opinion for PCT/EP2016/064221, mail date Dec. 9, 2016.
(Continued)

*Primary Examiner* — Shahdeep Mohammed
*Assistant Examiner* — Farouk A Bruce
(74) *Attorney, Agent, or Firm* — Andrus Intellectual Property Law, LLP

(57) ABSTRACT

A method for safe radioisotope preparation and injection of $H_2^{15}O$ for use in Positron Emission Tomography (PET). The disclosure also relates to a safety valve for controlling a flow of H215O for use in PET, to a use of said safety valve and to a method for preparing and injecting $H_2^{15}O$.

1 Claim, 8 Drawing Sheets

(51) Int. Cl.
    *A61B 6/42*    (2024.01)
    *A61M 5/14*    (2006.01)
    *A61M 5/36*    (2006.01)
    *A61M 39/22*   (2006.01)
    *F16K 11/085*  (2006.01)
    *G21G 1/00*    (2006.01)
    *G21G 1/10*    (2006.01)

(52) U.S. Cl.
    CPC ........ *F16K 11/085* (2013.01); *F16K 11/0853* (2013.01); *G21G 1/10* (2013.01); *A61B 6/037* (2013.01); *A61M 2039/226* (2013.01); *A61M 2039/229* (2013.01); *A61M 2205/33* (2013.01); *A61M 2205/3341* (2013.01); *A61M 2205/3379* (2013.01); *G21G 2001/0094* (2013.01)

(56) References Cited

U.S. PATENT DOCUMENTS

| | | | |
|---|---|---|---|
| 5,223,434 A | 6/1993 | Kanno et al. | |
| 5,482,865 A | 1/1996 | Ferrieri et al. | |
| 5,800,397 A | 9/1998 | Wilson et al. | |
| 8,602,058 B1 | 12/2013 | Del Castillo | |
| 9,500,287 B2 | 11/2016 | Duncan | |
| 2003/0060704 A1* | 3/2003 | Emig | A61M 5/1407 600/432 |
| 2005/0277833 A1 | 12/2005 | Williams, Jr. | |
| 2007/0213848 A1 | 9/2007 | Dekemp | |
| 2009/0131862 A1 | 5/2009 | Buck et al. | |
| 2010/0121184 A1* | 5/2010 | Dhawale | G21H 5/02 250/363.04 |
| 2011/0002802 A1 | 1/2011 | Capone | |
| 2011/0178359 A1* | 7/2011 | Hirschman | G21G 4/08 600/4 |
| 2012/0136334 A1* | 5/2012 | De Sausmarez Lintell | A61M 5/3294 604/500 |
| 2013/0211247 A1* | 8/2013 | Kalafut | A61B 6/507 703/11 |
| 2013/0261599 A1 | 10/2013 | Haueter et al. | |
| 2013/0277566 A1 | 10/2013 | Giamis | |
| 2014/0249349 A1 | 9/2014 | Marsh | |
| 2016/0151642 A1 | 6/2016 | Kim | |

FOREIGN PATENT DOCUMENTS

| | | |
|---|---|---|
| EP | 2457602 A1 | 5/2012 |
| EP | 2653863 A1 | 10/2013 |
| FR | 2286325 A1 | 4/1976 |
| JP | S49109942 | 10/1974 |
| JP | H5-119197 | 5/1993 |
| JP | H09173447 A | 7/1997 |
| JP | 2008506428 | 3/2008 |
| WO | 2005118031 A1 | 12/2005 |
| WO | 2006007750 A1 | 1/2006 |
| WO | 2008089985 A1 | 7/2008 |

OTHER PUBLICATIONS

Examination Report for corresponding European Application No. 18199616.6, dated Feb. 24, 2023.

Palmer B M et al. "An Automated [$^{15}$O]H"2O Production and Injection System for PET Imaging", Nuclear Medicine and Biology, Elsevier, NY, US. vol. 22, No. 2, Feb. 1, 1995. pp. 241-249.

Office Action for U.S. Appl. No. 17/324,251, dated Aug. 30, 2023.

Final Office Action for U.S. Appl. No. 15/738,032, dated Sep. 8, 2023.

* cited by examiner

SYSTEM FOR SAFE RADIOISOTOPE PREPARATION AND INJECTION

CROSS REFERENCE TO RELATED APPLICATIONS

The present application is a divisional application of U.S. patent application Ser. No. 15/738,032, filed Dec. 19, 2017, which is a U.S. national stage of International Application PCT/EP2016/064221, filed Jun. 20, 2016, which international application was published on Dec. 22, 2016 as International Publication No. WO 2016/203055. The International Application claims priority to European Patent Application No. 15172904.3, filed Jun. 19, 2015. The contents of each are incorporated herein by reference in their entireties.

FIELD

The present invention relates in a first aspect to a regulating means for a system for preparing and injecting H215O for use in Positron Emission Tomography (PET). The invention also relates in a second aspect to a system for preparing and injecting H215O, in a third aspect to a safety valve for controlling a flow of H215O for use in PET, in a fourth aspect to a use of said safety valve and in a fifth aspect to a method for preparing and injecting H215O.

BACKGROUND

Radioisotopes (also called radionuclides) have several applications in medical therapy, imaging and research. Through the emission of positrons from radioisotopes, PET permits imaging and measuring of physiological processes within the human body.

Radioisotopes such as 18F, 11C, 15O, 14O, 82Rb and 13N are typically used in labelling radiopharmaceuticals for use in PET. The half-life associated with these radioisotopes is very short, typically on the order of minutes (except 18F which has a half-life of almost two hours). Oxygen-15 (15O) has a half-life of 122.24 seconds and is one of the most suitable radioactive isotopes for use in PET for quantifying regional cerebral blood flow (rCBF), and for quantifying regional myocardial blood flow (rMBF).

Most systems for producing radioactive water comprise a cyclotron, which produces a target gas. The cyclotron target gas is transferred into a HotCell residing in a qualified laboratory environment, wherein it is converted from 15O-O2 into H215O using either a catalytic process or heating to approximately 800° C. in connection with infusion of H2. The converted H215O is then typically bubbled into a saline solution in a reservoir, thus trapping the H215O in said solution. The H215O-solution is then manually transferred from the reservoir into a draw up room or similar, and the desired dose for the patient is then typically manually drawn up into a syringe, which is then manually transported into a PET-scanning room.

Due to the short half-life of 15O, it is only possible to use 15O in a system that both produces and injects radioisotopes directly into the patient. Therefore 15O is only used to a limited extent in for example research purposes or under special waivers, due to the security aspect with regards to the patient being directly connected to the system.

A key aspect of the safety considerations in a system that both produces and injects radioisotopes into patients is the flow through of compressed gas. At one end of such systems a cyclotron is connected and delivers compressed radioactive gas, which is pressurized to 10 atm or more. At the other end of the system a patient is connected, often through a peripheral venous catheter, establishing a direct connection between the patient and the compressed radioactive gas.

Standard safety features typically consist of the gas passing on one side of a semi-permeable membrane and saline passing on the other side. Immediately before the patient a sterile filter made of a similar material as the first semi-permeable membrane will be located. The sterile filter will gas-lock in the event that any gas passes through the first membrane, but if a gas waste tube leading the gas away is blocked, the pressure may rise to a higher pressure than the membrane can handle, which may allow the gas to pass through both filters and into the patient. The result could be the infusion of radioactive gas into the patient from several hundred ml/minute up to 1-2 l/minute, which may cause fatal venal air embolisms.

In known valves used for such systems, the valve can be configured to have a venting opening, wherein to release excess fluid from the system, the valve has to be turned to a configuration where a flow path through the valve is established between the incoming fluid and the venting opening. This requires manually or automatically turning the valve to said configuration, and it will thus not function as a safety valve if a malfunction occurs in the system.

Further, the system operating with compressed gas deal with the fundamental problem of requiring a fail-safe feature ensuring that compressed gas cannot enter other parts of the system, thereby possibly influencing or damaging them.

To minimise the level of risk for the patient, the manual transferal of the radioisotopes from a reservoir by syringe to the patient is performed by medical personnel. This way the patient is not connected to the cyclotron, either directly or indirectly, thereby abating the risk of being infused accidentally by radioactive gas.

The manual handling of the radioisotopes is safe with regards to the patient, but due to the repeated radioactivity exposure to the medical personal, it is not feasible for routine patient examinations, since the medical personal is subjected to unwanted and dangerous radiation with every extraction and injection performed.

Typically, under the manual regime the double amount of desired radioactivity is measured in a dose calibrator and extracted. A timer is started, and when the radioactivity has decreased due to the decay of the relevant radioisotope and reached the desired level, the extracted amount is transferred to the patient. Because of the short half-life of the radioisotopes the timing of the extraction and injection has to be very precise to determine the actual amount of radioactivity transferred to the patient.

Thus, there is a need for at system that is capable of both producing and injecting specified amounts of H215O with high precision and with a negligible risk for both patients and medical personnel.

SUMMARY OF THE INVENTION

On this background the object of the invention is to provide a regulating means, a system, a safety valve and a method with enhanced safety features for preparing and injecting H215O in a saline solution.

With the third aspect of the invention this object is achieved by providing a safety valve for controlling a flow of H215O for use in Positron Emission Tomography, the valve comprising: a valve element with a flow channel extending through the valve element, a valve housing with at least three valve openings, each valve opening allowing fluid flow into or out of said valve, and at least two overflow recesses, each with at least one outlet opening, wherein the valve element and valve housing are connectable to form an assembled valve, the valve element and the valve housing being in contact with each other in a contact area, wherein the assembled valve can be arranged in at least two, different open configurations, one of said open configurations defining a flow path through the flow channel and one set of said valve openings, and another of said open configurations defining a flow path through the flow channel and another, different set of said valve openings, and wherein in each of said at least two open configurations: each overflow recess is arranged between the valve element and the valve housing, at least two of the valve openings are connected by the flow channel, at least one of the valve openings is not connected to the flow channel, said contact area forms a fluid block preventing fluid flow into said at least one valve opening not connected to the flow channel, the overflow recesses are not in fluid communication with the flow channel, each overflow recess is positioned to establish an interruption of said contact area so that the overflow recesses establish safety relief vents that vent overflow fluid, which in case of overpressure passes through said fluid block, through said respective outlet openings, so that in said at least two open configurations said overflow fluid is prevented from entering into said at least one valve opening not connected to the flow channel.

By providing a valve comprising said at least two overflow recesses, the overflow recesses ensures that no fluid will travel from the at least two valve openings connected by the flow channel to the at least one valve opening that is not in connection with the flow channel, when the assembled valve is arranged in the at least two different open configurations, since the fluid will be vented through the overflow recesses and away from the valve.

The assembled valve may be arranged in a closed configuration, wherein the flow channel is not connected to any of the valve openings, so that no flow path through the flow channel and valve openings is established. In this closed configuration excess pressure of fluid present in the valve openings may also arise. If the fluid passes through the fluid block, the overflow recesses vents the overflow fluid through said respective outlet openings.

Since the pressure in the overflow recesses is lower than the pressure integrity of the adjacent valve openings, the pressure difference ensures that overflow fluid will be vented out from the valve.

Thereby the valve functions as a safety valve preventing undesired pressurized fluid from entering valve opening(s), where it is not intended to enter.

In the context of this application it is to be understood that pressurized fluid may also be fluid at atmospheric pressure (around 1.01325 bar). Preferably the fluid is at approximately 1 to 3 bar, preferably 1.5 to 2.5 bar, more preferred approximately 2 bar, when said system functions under normal conditions.

It is also to be understood that "undesired" fluid refers to but not limited to both fluid that is not intended to pass from one opening of the valve to another, when the valve is in the closed configuration, whatever the pressure of the fluid may be, and to fluid that due to for example a malfunction in the system prior to the valve has been pressurized to an undesired higher pressure than intended. And vice versa the term "desired" fluid refers to fluid that under normal functioning conditions is intended to pass through the valve in an open configuration.

Under this normal functioning condition of the system, and when the valve is arranged in an open configuration where the flow channel is connected to the valve openings, the amount of fluid that passes though the valve is in the range of approximately 500-1000 ml/min.

When the desired fluid passes through the flow channel and valve openings the fluid may be around atmospheric. No significantly pressure drop is present when the fluid passes normally through the flow channel and valve openings.

When the valve is arranged in a system for preparing and injecting $H_2{}^{15}O$ in a saline solution, the valve will function as a safety valve and will thus prevent undesired pressurized fluid from reaching and harming a patient that is fluidly connected to the system.

The safety valve will ensure, that in the case where a malfunction occurs prior to the valve in functional terms of the system, the malfunction for example resulting in a undesired high pressurized fluid reaching an opening of the valve, and the flow channel of the valve not being connected to any of the valve openings, the fluid will be vented out from the valve through the overflow recesses and will not enter the other valve openings.

The same applies for the situation where the valve is in an open position and a patient is connected to a connection element of the valve, the valve opening of said connection element not being in fluid connection with the flow path. Here the fluid will flow between the valve openings and the flow path and if a malfunction occurs, and undesired pressurized fluid enters the valve openings and flow path, the overflow fluid that will enter the contact area between the valve element and the valve housing, will be vented out through the recesses, that are position between the valve opening of the connection element connected to the patient and the valve openings in connection to the flow path.

Thus the recesses will function as a safety measure irrespective of the configuration of the valve and without the need to shift between configurations increasing the safety of the patient connected to the system.

Therefore in an embodiment the assembled valve can be arranged in a third different closed configuration where the flow channel is not connected to any of the valve openings, so that no flow path through the flow channel and valve openings is established.

The contact area between the valve element and the valve housing should be understood as an area where a surface of the valve element is directly adjacent to a surface of the valve housing. The fluid block in the contact area ensures functional tightness between the valve housing and the valve element.

In the context of this application the term "connected" may also be understood as a fluid connection and/or being in fluid communication.

In the context of this application the term "fluid" comprises both gases and liquids.

The at least three valve openings may have any shape which permits a flow of fluid from one side of the opening to another. The valve openings are preferably circular.

The valve housing and/or valve element may be of any desirable shape such as for example cylindrical, circular, rectangular or spherical.

The dimensions of the valve element may vary according to the dimensions of the valve housing.

The safety valve may be formed from a material chosen from the group consisting of inert materials, polymer materials, metals and metal alloys and ceramics or made from a combination of such materials. Any material that is compatible with the fluid, has sufficient strength and material properties to provide a tight fluid block and is able to withstand sterilization may in principle be used.

Depending on the material of the safety valve, the valve may be produced by methods such as injection molding, lathe processing, milling, casting and/or 3D printing.

The valve element and valve housing may be made from different material compositions. By constructing the valve element and valve housing in different material compositions a tighter fit may be obtained. The valve element may be formed by a material having a lower material strength than the material of the valve housing to achieve a selected rupture of the valve element rather than the valve housing during an accidental pressure rise.

In an embodiment the valve housing further comprises a connection element having a first and a second end and an internal fluid space, the connection element being connected to the valve housing at the second end, so that said fluid space is in fluid contact with one of said at least three valve openings.

By providing a connection element it is easy to connect the safety valve directly to different medical systems, in which systems valves are utilized to prevent pressurized fluid from entering, for example, a patient's veins or arteries and where it therefore is desired to enhance the safety of the system to ensure that no overflow fluid will travel to undesired valve openings. Such a medical system may be a system for preparing and injecting H215O, where the safety valve will ensure that overflow fluid will not be transferred to a patient line and an unintended infusion of fluid into a patients circulatory system posing a potentially life threatening situation is avoided.

In an embodiment the connection element is cylindrical. The at least three connections elements may extend radially from the shell. The at least three connections elements may be of approximately equal length.

In an embodiment the valve housing comprises three connection elements.

In an embodiment the at least two overflow recesses are arranged in the valve housing.

In an embodiment the at least two overflow recesses are arranged in the valve element.

The overflow recesses may be of any shape such as curved or twisted. The overflow recesses are preferably linear.

By providing the at least two overflow recesses in the valve housing and/or in the valve element, an easily assembled valve is provided, with a minimum number of components, making the valve cost effective and easy to produce and assemble.

In an embodiment the valve element further comprises a first end and a second end defining a first longitudinal axis, and the valve housing further comprises; a shell comprising a first end and a second end and a second longitudinal axis extending between the first and the second end, the second longitudinal axis being coaxial with the first longitudinal axis, an internal spacing for receiving the valve element, said internal spacing being enclosed by the shell, and the at least three valve openings being arranged in the shell, each opening allowing fluid flow into or out of the internal spacing, wherein the at least two overflow recesses extends axially between said first and second ends of the shell, wherein the valve element is axially movable along the second longitudinal axis, so that a part of the valve element is insertable into the internal spacing of the valve housing to form the assembled configuration and the valve element is rotatable inside the internal spacing around the second longitudinal axis, so that the valve element and valve housing can change between said least two different open configurations, wherein when the valve element is arranged inside the internal spacing in said two different open configurations, each overflow recess is arranged between the valve element and the shell.

By providing the safety valve with a valve element that can be inserted into the valve housing, it is possible to secure the valve element inside the valve housing preventing the valve element from moving in the radial direction with respect to the first longitudinal direction, thereby establishing a very high functional tightness in the contact area and thus a better fluid block for preventing any excess fluid from passing the contact area.

The valve housing may be rotatable around the valve element around a first longitudinal axis 124 of the valve element, when part of the valve element is inserted into the internal spacing.

The rotation of the valve element and/or valve housing may be automated and/or manual.

In an embodiment the valve housing comprises three valve openings.

In an embodiment the safety valve comprises three overflow recesses.

In an embodiment the valve element comprises one flow channel.

In an embodiment the number of valve openings is equal to the number of overflow recesses.

In some embodiments the valve housing comprises six valve openings and/or six overflow recesses. The six valve openings and/or six overflow recesses are preferably evenly distributed in the circumference of the valve housing and/or valve element.

In an embodiment the at least three valve openings are distributed equally in the shell. An angle between each of the valve openings with respect to the neighbouring valve opening is preferable 120 degrees.

In an embodiment the flow channel comprises a first flow channel and a second flow channel, where the first and second flow channels extend at an angle with respect to each other. The angle is preferably 120 degrees.

By providing the valve openings and the first and second flow channels at an approximately equal angle, then when the valve element is arranged inside the internal spacing, the first and second flow channels through the valve element will coincide with two of the at least three valve openings of the valve housing, so that two of the at least three valve openings may be connected by the flow channel.

In an embodiment the at least two overflow recesses are arranged in the shell.

In an embodiment the at least two overflow recesses extends between and opens into the first and second ends of the shell.

In an embodiment the at least two overflow recesses extends between and opens into the first and/or second ends of the shell.

The overflow recesses may extend radially in the shell, the overflow recesses having a depth up to the thickness of the shell.

In an embodiment the at least two overflow recesses are arranged in the valve element.

In an embodiment the at least two overflow recesses extends between and opens into the first and/or second ends of the valve element.

By providing overflow recesses extending for the entire length of the shell or valve element, the overflow recesses ensures that any fluid travelling along the fluid block between the valve element and the valve housing will be vented out of the valve through the overflow recesses.

In an embodiment the connection element extends into the internal spacing.

In some embodiments the overflow recesses may comprise a material that has different material properties than a material of the shell. This is advantageous when the valve is used in systems which handles high pressure and/or is constructed of high strength materials such as metals or metal alloys or ceramics.

In an embodiment the shell is cylindrical.

In an embodiment the valve element is cylindrical.

By providing a cylindrical shell and/or valve element a good balance between the amount of material used and the strength and stiffness of the entire valve is ensured.

In an embodiment the flow channel and the at least three valve openings are arranged and extending in the same plane in the at least two configurations of the assembled valve.

Thus the safety valve can be arranged without the need for much space, since the inlets and outlets are all arranged in the same plane, instead of having an inlet that is perpendicular to the flow channel/valve openings In an embodiment said plane is approximately perpendicular to the first and second axis, when the valve is in the assembled configuration.

It is to be understood that a plane is a flat, two-dimensional surface that extends infinitely far, and that the flow channel and valve openings are positioned on the same plane and extending in different directions in that same plane.

In an embodiment the overflow fluid is at approximately 1-10 bar, preferably approximately 1 to 5 bar and more preferred approximately 1 to 3 bar.

In an embodiment the valve openings are equally distributed around a circumference of the shell, the valve openings preferably being distributed at an angle of approximately 120 degrees.

An inner circumference of the shell may be approximately equal to an outer circumference of the valve element.

The valve element comprises a first end and a second end, which defines a first longitudinal axis. The valve housing comprises a first end, a second end and a second longitudinal axis extending between the first and the second end. The second longitudinal axis is coaxial with the first longitudinal axis of the valve element, when the valve is in the assembled configuration.

In an embodiment the valve element comprises a handle for rotating the valve element inside the valve housing.

When the safety valve is assembled the valve element may be rotated inside the valve housing, the rotation being around the second longitudinal axis.

The handle may protrude from the valve element being outside the shell when a part of the valve element is inserted into the internal spacing. The handle preferably extends radially from the valve element.

In an embodiment the handle comprises a first, second and third protrusion extending radially from the valve element. The first and second protrusions are preferably arranged in the circumference of the valve element at an angle of 90 degrees with respect to each other. The second and third protrusions are preferably arranged in the circumference of the valve element at an angle of 90 degrees with respect to each other.

The handle may be a depression into the valve element. Said depression may be constructed such as having the shape of a square, triangle, circle, oval, rectangle, star or any combinations there off.

In an embodiment the valve housing further comprises a sterile filter element, the filter being arranged so that any overflow fluid vented from the overflow recesses passes through the filter element. The filter element may be arranged at the first and/or second end of the shell.

In a further embodiment the filter covers the entire at least one outlet opening of each of the at least two overflow recesses.

In a further embodiment the at least two overflow recesses are arranged in the shell and extends between the first and the second ends of the shell. The at least one outlet opening is arranged in the second end of the shell, so that the overflow recesses opens into the second end of the shell, where the filter element is arranged inside the internal spacing at the second end of the shell. Thus vented fluid will only exit the safety valve at the second end of the shell and thereby all vented fluid will pass through the sterile filter before being vented from the safety valve.

The filter further prevents any contaminated air from the valve surroundings from entering the safety valve.

The filter element may have any suitable shape. The filter element may have the same shape as the internal spacing and is preferably circular.

The filter element may be formed from a material chosen from the group consisting of porous polymer membranes, sintered particles or fibres made from polymers, metals or ceramics or made from a combination of such materials.

The filter element may have a pore size of 0.10 to 100 um, preferably 0.2 to 0.45 um.

The filter element may be HEPA filter.

In a fourth aspect the invention related to a use of a safety valve as described above in relation to the third aspect in a system for preparing and injecting H215O in a saline solution.

The system may be according to a second aspect of the system as described below.

By providing the safety valve in such a system, then if a malfunction of the system occurs, the malfunction possibly leading to fluid at unwanted high levels in the tubes that the patient is connected to, then the safety valve will protect the patient from being harmed by the unwanted fluid.

In a second aspect the invention relates to a system for preparing and injecting H215O for use in Positron Emission Tomography (PET), said system comprising; producing means for producing a saline solution of H215O, bolus means for establishing a first bolus for injection, said first bolus comprising said saline solution of H215O and having a predefined volume and radioactivity concentration (mBq/ml), said bolus means comprising a valve, and regulating means for regulating an injection profile of the first bolus.

As used herein the term "oxygen-15 labelled water" is denoted as H215O covering similar denotations such as 015-H2O, O15-H2O, H2[15O], H2O[15O] and 15OH2O.

By providing a system according to the invention for preparing and injecting H215O that may be arranged next to the PET-scanner, the need for manual handling of radioisotopes is eliminated, thus improving the safety for both patient and medical staff.

Further, since the system operates continuously it is possible to make dose injection precisely at a time of interest. This enables time critical studies such as brain activation and cardiac stress studies. The system supports various study protocols by offering different infusion boluses.

According to the second aspect of the invention it is possible to precisely determine the amount of radioactivity that is prepared, since the H215O is prepared in a predefined bolus, and to define and regulate the injection profile, i.e. the time-dependent injection speed, which defines the amount of radioactivity injected during the injection period. In some embodiments the injection speed is constant throughout the injection period. In this way the radioactivity and the bolus volume will be well defined.

In some embodiments the injection speed varies throughout the injection period.

As used herein the term "bolus" means a specific volume quantity.

As used herein the term "injection profile" means a graph in an XY diagram in which the Y-axis represents the radioactivity concentration as a function of time [Bq/s] and the X-axis represents time [s].

In an embodiment the system according to the second aspect comprises a processing unit.

Here and in the following, the term 'processing unit' is intended to comprise any circuit and/or device suitably adapted to perform the functions described herein. In particular, the above term comprises general purpose or proprietary programmable microprocessors, Digital Signal Processors (DSP), Application Specific Integrated Circuits (ASIC), Programmable Logic Arrays (PLA), Field Programmable Gate Arrays (FPGA), special-purpose electronic circuits, etc. or a combination thereof.

The processing unit may be connected to the producing means and/or the bolus means and/or the regulating means and/or the entire system according to the second aspect and/or specific parts thereof.

In an embodiment said valve is a safety valve according to the third aspect of the invention.

The system may be connected to a patient, so that the bolus can be injected directly from the system and into the patient. The bolus may be administered intravenously, intramuscularly, intrathecally or subcutaneously.

Parts of the system may be arranged within or behind a radiation shield.

In a embodiment the invention involves a producing means for a system according to the second aspect, the producing means comprising; a converting element for converting a gas mixture comprising 15O and H2 to H215O under increased temperature, a valve control element for regulating a flow of said gas mixture, a combining means for combining H215O with saline from a first saline feed to produce a saline solution of H215O, a first radiation detector for measuring the radioactivity in said saline solution of H215O, wherein said valve control element is regulated by the first radiation detector.

A gas mixture comprising 15O and H2 is fed at a constant flow rate and pressure to the producing means according to the embodiment. The provided valve control element makes it possible to regulate the amount of gas mixture that is converted to H215O, and thereby the concentration of H215O in the saline solution of H215O.

The gas mixture may comprise a compressed or pressurized mixture of gases.

The gas mixture is preferably converted to H215O in vapour form.

The radiation detector may comprise a controlling part for comparing the measured amount of radiation with a predefined radiation interval, said interval depending on the desired amount of H215O in the saline solution. The interval may be manually and/or automatically entered depending on the desired amount of H215O, which may vary from patient to patient. The controlling part may be controlled by a processing unit.

In an embodiment the converting element comprises an oven that converts the gas mixture to H215O under increased temperature.

The increased temperature may be 200-1000° C., preferably approximately 800° C. for an uncatalyzed reaction and approximately 300° C. for a Pd-catalyzed reaction.

In an embodiment the valve control element comprises at least one valve for directing the gas mixture flow either through the converting element, thereby converting the gas mixture to H215O, or bypassing the converting element whereby the gas mixture will not be converted to H215O, when it is not desired to produce any more H215O.

In a further embodiment the at least one valve is a two-way valve.

In a further embodiment the at least one valve is a safety valve according to the third aspect of the invention In a further embodiment the valve control element also comprises a third gas waste. The at least one valve directs the gas mixture either to the oven or the oven is bypassed and the gas is directed into the third gas waste.

The third gas waste may be a slow seeping gas waste. The third gas waste may alternatively be an external ventilation pipe specific for the venting of the gas mixture.

In an embodiment the combining means comprise; a reservoir for receiving H215O and the first saline solution, a second gas waste for venting any excess gas from said reservoir, a third pump being connected at one end to the reservoir and at another end to a decay line, the decay line being connected to a liquid waste, wherein the third pump pumps excess liquid waste from the reservoir through the decay line and into the liquid waste, By providing the combining means, which is not pressurised/operates at normal pressure, an additional safety feature is provided to ensure that no gas is dissolved in the radioactive water.

It is noted that in the context of the present specification the term "reservoir" is not limited to being a specific reservoir but may also be other containers with a predefined volume such as tanks, basins, store/deposit elements, vessels or receptacles.

It is noted that in the context of the present specification the term "slow seeping gas waste" refers to a system which allows excess gases containing small amounts of radioisotopes like e.g. 15O to be delayed for a suitable number of half-life periods, preferably at least five half-life periods, before the excess gas is vented to the open, such that the residual radioactivity has decreased to acceptable levels. The slow seeping gas waste will typically be located behind a radiation shield.

The second gas waste may be a slow seeping gas waste. The second gas waste may alternatively be an external ventilation pipe specific for the venting of the excess radioactive gases. Because of the short half-life of 15O and the small volumes of gas involved, the radioactivity is almost zero, when the gas is vented out.

The gas mixture comprising 15O and H2 fed to the converting element may contain small amounts of nitrogen oxides (NOx) which through a reaction with hydrogen are reduced to ammonia (NH3). The pH of the saline solution of H215O in the reservoir will thus increase if there is a build-up of ammonia.

In an embodiment the combining means further comprise a first pump connected to the first saline feed for providing the reservoir with the saline solution, and a pH-measuring device connected to the decay line, wherein the first pump is regulated by the pH-measuring device.

The amount of the first saline solution from the first saline feed may be an adjustable amount. The amount of the first saline solution may be manually and/or automatically adjusted by the processing unit.

The first saline solution may be continuously pumped into the reservoir.

By providing a pH-measuring device, the measuring device may detect changes in a pH-value of the saline solution of $H_2^{15}O$. These changes may happen if a high amount of ammonia is present in the saline solution of $H_2^{15}O$.

To secure that no build up of ammonia takes place in the reservoir, the inflow of saline solution and outflow of the saline solution of $H_2^{15}O$ may be regulated so that ammonia is washed out of the reservoir.

The content of ammonia in the reservoir should be below 15 ppm, preferably below 10 ppm. The pH-level in the reservoir should be from 4-10, preferably from 5-9, more preferred from 5.5-8.5.

Providing a relatively long decay line allows the radioactive $H_2^{15}O$ to decay before reaching the waste bottle. The radioactive $H_2^{15}O$ will preferably be delayed for at least five half-life periods before reaching the waste bottle.

The waste bottle may be placed outside the radiation shield arranged around the system. A radiation detector may also be arranged adjacent to the decay line or waste bottle.

The pumping speed of P3 is larger than or equal to the pump speed of P1 to ensure that the reservoir of saline solution of $H_2^{15}O$ does not overflow.

Any excess gas present in the reservoir is vented through a second gas waste. The second gas waste may be a slow seeping gas waste.

In an embodiment the invention involves a bolus means for a system according to the second aspect, wherein the bolus means comprise; a reservoir comprising a saline solution of $H_2^{15}O$, a conveying tube for circulating the saline solution of $H_2^{15}O$ from the reservoir through a loop element and a regulating device and back into said reservoir, a second pump for regulating said flow, wherein the regulating device comprises a valve, the regulating device having a first and a second configuration, where the second configuration of the regulating device establishes a first bolus of said saline solution of $H_2^{15}O$, the first bolus having a predefined volume and radioactivity concentration.

By providing a continuously circulating, readily available saline solution of $H_2^{15}O$, the system is at any point in time ready for establishing a first bolus for injection into a patient, thereby avoiding unnecessary waiting time.

The reservoir may comprise a saline solution of $H_2^{15}O$ produced according to an embodiment of the invention.

Further, since the saline solution of $H_2^{15}O$ is constantly being circulated in the conveying tube by the second pump at a high speed from and to the reservoir, in which reservoir newly formed $H_2^{15}O$ is constantly being mixed with saline, the saline solution of $H_2^{15}O$ available in the loop element will maintain an approximately constant radioactivity concentration.

The speed of the second pump is preferably from 0.1 to 100 ml/min.

In an embodiment the bolus means comprise a processing unit.

The regulating device may be manually controlled and/or automatically controlled by the processing unit.

In an embodiment the regulating device comprises at least two valves.

In an embodiment the regulating device comprises a safety valve according to the third aspect of the invention.

In an embodiment at least two valves are arranged one either side of the loop. One of the two valves may be connected to a patient line.

By using the safety valve according to the third aspect of the invention, no overflow liquid will enter the patient line, ensuring a safer system.

In an embodiment the loop element has an adjustable volume. The volume of the loop element may be adjusted manually and/or automatically by the processing unit. The volume of the loop element may also be adjusted by changing a part or a plurality of parts of the loop element giving the loop element one volume with a different part or plurality of parts resulting in the loop element having another volume.

Thus different bolus volumes and radioactivity concentration may easily be provided for use with different patients and/or measurements, thereby eliminating the need for manually extracting a bolus by medical personnel.

In an embodiment a first radiation detector is arranged adjacent to the loop element, the first radiation detector comprising a first and a second detector unit, wherein said first and second detector units measures a first and a second radioactivity value of said saline solution of $H_2^{15}O$ present in the loop element.

The first and second detector units are preferably arranged at different positions adjacent to the loop element, thus the detectors measure the first and second radioactivity values of said saline solution of $H_2^{15}O$ at different positions in the loop element. The first radiation detector may be separately shielded to yield precise radiation measurements.

In a first aspect the invention involves a regulating means for a system according to the second aspect, the regulating means comprising; a second saline feed, a loop element comprising a first bolus of said saline solution of $H_2^{15}O$, an injection means for collecting a predefined second bolus of saline from said second saline feed and injecting said second bolus at a predefined speed into the loop element, so that the second bolus pushes the first bolus into a patient line, a second radiation detector adjacent to the patient line, said radiation detector measuring a injection profile of said first bolus, wherein said injection speed and volume of the second bolus regulates the injection profile of the first bolus.

By providing the injection means it is possible to regulate the injection profile of the first bolus for injection into the patient line depending on individual requirements for different measurements.

In an embodiment the regulating means according to the first aspect comprise a processing unit.

The predefined injection speed may be altered during the injection. The speed is preferably lowered during the injection. The change in said speed may be controlled manually or by the processing unit.

The predefined second bolus of saline may have a variable volume depending on different patients and measurements. The predefined second bolus may be manually collected and/or automatically collected by the injection means. The automatic collecting may be controlled by the processing unit.

In an embodiment the injection means comprise a fourth valve. The fourth valve may be a safety valve according to the third aspect of the invention.

The second saline feed may be connected to the fourth valve.

In an embodiment the injection means comprise a collecting element. The collecting element may be connected to the fourth valve. The collecting element may be a medical syringe.

The second detector measures the radioactivity value of a specific part of the patient line. This part has a known length, size and volume. Since the volume of this part of the patient line is constant, the radioactivity is measured at short time intervals (1-10 measurements per second) and the injection speed is known, it is possible to obtain a curve in an XY-coordinate system, referred to herein as the injection profile, which shows the injected amount of activity as a function of time.

The second radiation detector measures the injection profile of the first bolus immediately before injection into the patient.

In a fifth aspect the invention involves a method for preparing H215O for use in Positron Emission Tomography, said method comprising the steps of; converting a gas mixture flow comprising 15O and H2 to H215O under increased temperature, providing a valve control element for regulating a flow of said gas mixture, combining H215O with saline from a first saline feed to produce a saline solution of H215O, providing a first radiation detector for measuring the radioactivity in said saline solution of H215O, regulating said gas mixture flow with the first radiation detector, providing a reservoir for receiving the saline solution of H215O, providing a second gas waste for venting any excess gas from said reservoir, providing a third pump, the third pump being connected at one end to the reservoir and at another end to a decay line, the decay line being connected to a liquid waste, pumping with the third pump any excess liquid waste from the reservoir through the decay line and into the liquid waste, providing a conveying tube and a second pump for circulating the saline solution of H215O from the reservoir through a loop element and back into said reservoir, providing a regulating device, establishing a first bolus of said saline solution of H215O in the loop element, the first bolus having a predefined volume and radioactivity concentration, providing a second saline feed, collecting a predefined second bolus of saline from said second saline feed, injecting said second bolus at a predefined speed into the loop element, so that the second bolus pushes the first bolus into a patient line, measuring with a second radiation detector adjacent to the patient line a injection profile value of said first bolus, regulating the injection profile of the first bolus with said injection speed and volume of the second bolus.

In an embodiment of the fifth aspect the regulating device comprises a safety valve according to the third aspect of the invention.

A production-to-patient system for preparing and injecting radioisotopes presents a number of challenges. The need for safety in such a system, that may be connected to a patient, is extremely high, both ensuring the safety of the patient and the medical personal. By providing a system according to the second aspect the different parts of the system help ensuring a higher safety standard than previously possible.

The safety valve according to the third aspect is especially useful in a system according to the second aspect, as it will prevent overflow fluid from moving forward in the system and ultimately into the patient. Especially excess gases are a very high risk factor, which can be easily eliminated by implementing the safety valve according to the third aspect.

The different aspects of the present invention can be implemented in different ways, each giving rise to one or more of the benefits and advantages described in connection with at least one of the aspects described above, and each having one or more preferred embodiments, including the embodiments described in connection with at least one of the aspects above and/or disclosed in the dependent claims.

BRIEF DESCRIPTION OF THE DRAWINGS

The above and/or additional objects, features and advantages of the present invention will be further outlined by the following illustrative and non-limiting detailed description of embodiments of the present invention, with reference to the appended drawings, wherein.

DETAILED DESCRIPTION

In the following description, reference is made to the accompanying figures, which show by way of illustration how the invention may be practiced. Note that for illustrative purposes the dimensions of especially distances between various elements shown are deceptive.

It is to be understood that the terms "safety valve" and "valve" are used in the content of this invention as both describing the safety valve according to the third aspect of the invention.

Figure 1:
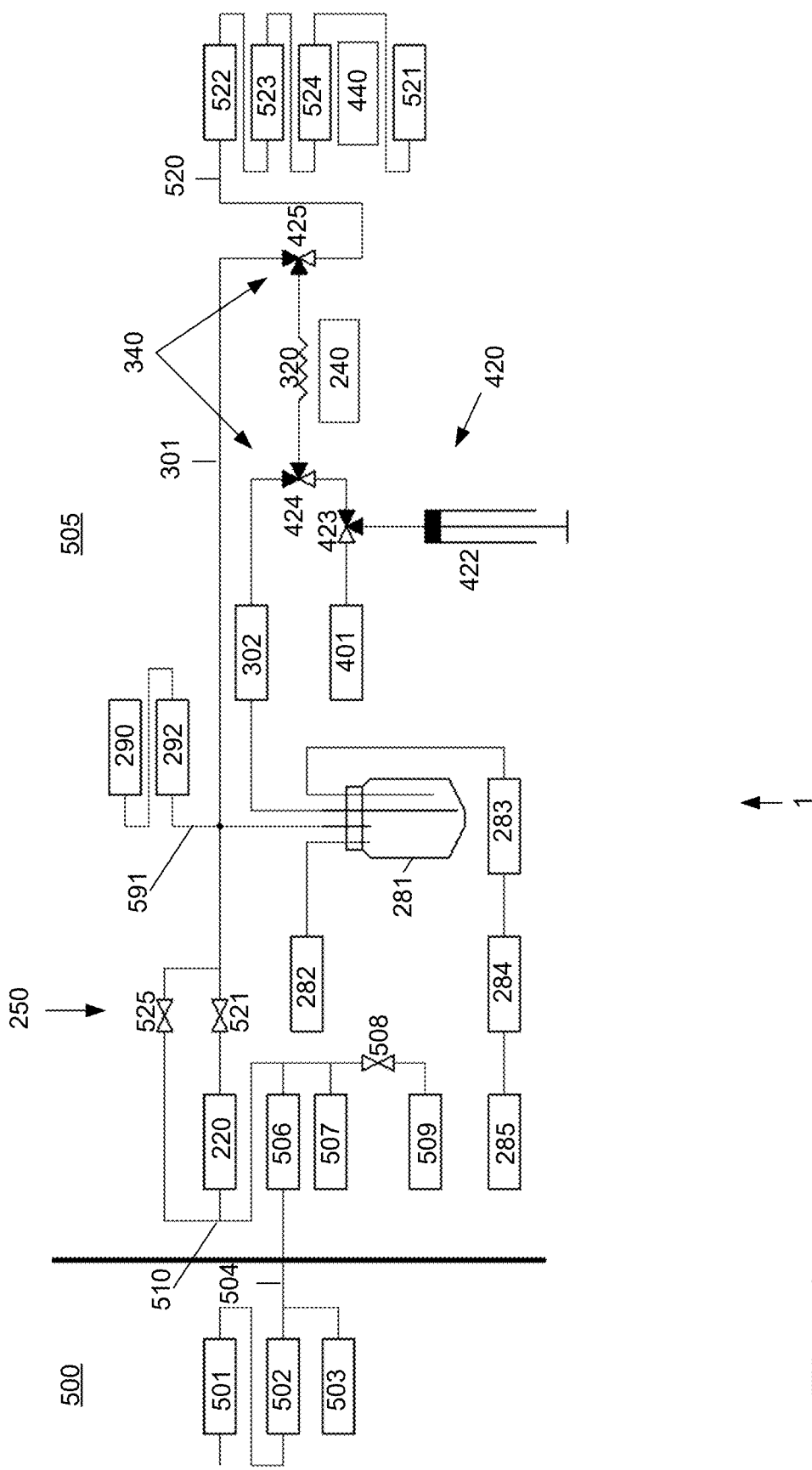
FIG. 1 shows a schematic diagram of a system for preparing and injecting H215O for use in Positron Emission Tomography according to the second aspect of the invention.

FIG. 1 shows a schematic chart of a system 1 embodying the present invention for preparing H215O in sterile injectable form for use in performing PET scanning.

The system 1 comprises a processing unit for controlling various parts of the system. The processing unit may be manually overridden if desired.

Here and in the following, the term 'processing unit' is intended to comprise any circuit and/or device suitably adapted to perform the functions described herein. In particular, the above term comprises general purpose or proprietary programmable microprocessors, Digital Signal Processors (DSP), Application Specific Integrated Circuits (ASIC), Programmable Logic Arrays (PLA), Field Programmable Gate Arrays (FPGA), special-purpose electronic circuits, etc. or a combination thereof.

Radioactive 15O-gas is produced in a cyclotron in a cyclotron vault 500 by conventionally irradiating a flowing gas target of nitrogen gas and oxygen gas. The amount of 15O-gas that is released from a cyclotron target chamber 501 is controlled by a Mass Flow Controller (MFC) (not shown) located in connection to the target chamber 501. The MFC is preset to control the gas at a particular range of flow rates.

The MFC is fitted with a closed loop control system which is given an input signal by a system operator or a processing unit that it compares to the value from the mass flow sensor and adjusts the proportional valve accordingly to achieve the required flow.

The 15O-gas is then passed through a NOx trap 502, where the majority of the nitrogen oxides such as NO, N2O and/or NO2 formed in the target chamber 501, by reaction between nitrogen and oxygen, are captured. It is desirable to remove nitrogen oxides already at this point, since they subsequently may be converted to unwanted ammonia (NH3) by reaction with hydrogen.

The gas is subsequently mixed with hydrogen (H2) gas from a hydrogen reservoir 503 to form a gas mixture 221 of H2 and 15O-gas. The amount of H2-gas that is mixed with the 15O-gas is controlled by another MFC (not shown) located after the hydrogen reservoir 503.

The gas mixture 221 is then led through a tube 504 extending from the cyclotron vault 500 and into a PET scanning room 505, where the PET scanner (not shown), patient 521 and the invention according to the second aspect are arranged. To avoid high pressure that may cause erratic flow rates, the tube 504 is fitted with a pressure relief valve (not shown).

The gas mixture 221 is then passed through a first sterile filter 506 to remove any unwanted particulate and microbial impurities to ensure that the system remains sterile.

After the first sterile filter 506 a pressure sensor 507 and a pressure relief valve 508 is connected to the gas transporting tube 504. The pressure sensor 507 continuously measures the pressure in the tube 504. If the pressure exceeds a predetermined safety level the valve 508 directs the gas mixture 221 to a first gas waste 509.

The gas mixture 221 is then directed to a tube junction 510. A valve control element 250 controls which way the gas mixture 221 is directed from the tube junction 510. The valve control element 250 comprises a second valve 521 and a third valve 525.

When the second valve 521 is open the gas 221 is directed through a converting element 220. The converting element 220 is an oven 220 wherein the gas mixture 221 is converted to H215O. If the second valve 521 is closed and the third valve 525 is open the gas mixture 221 will bypass the oven 220 and the gas mixture 221 will not be converted to H215O. This is done when it is not desired to produce any more H215O.

The gas mixture 221 from the third valve 525 and/or the H215O from the second valve 521 are then led into a reservoir 281. A first pump 292 connected to a first saline feed 290 continuously pumps a first flow 591 of saline into the reservoir 281. Thus the H215O and the saline are combined to a saline solution of H215O in the reservoir 281.

A first radiation detector 240 is located elsewhere in the system. The first radiation detector 240 measures the radioactivity in said saline solution of H215O. The signal from the first radiation detector 240 is used as input in a closed loop regulation algorithm such as PID or Fuzzy Logic executed on the processing unit. The output from the processing unit regulates said valve control element 250 and thus determines how much H215O is produced.

A second gas waste 282 is connected to the reservoir 281. The second gas waste 282 vents gas from said reservoir 281, thus ensuring that no gas is dissolved in the saline solution of H215O.

A third pump 283 is connected at one end to the reservoir 281 and at another end to a decay line 284. The decay line 284 is further connected to a liquid waste 285. The third pump 283 continuously pumps excess liquid waste from the reservoir 281 through the decay line 284 and into the liquid waste 285.

The reservoir 281 is also connected to a conveying tube 301 for circulating the saline solution of H215O from the reservoir 281 and back into the reservoir 281. The saline solution of H215O is pumped in the conveying tube 301 from the reservoir 281 by a second pump 302 and into a regulating device 340 and a loop element 320.

Figure 5:
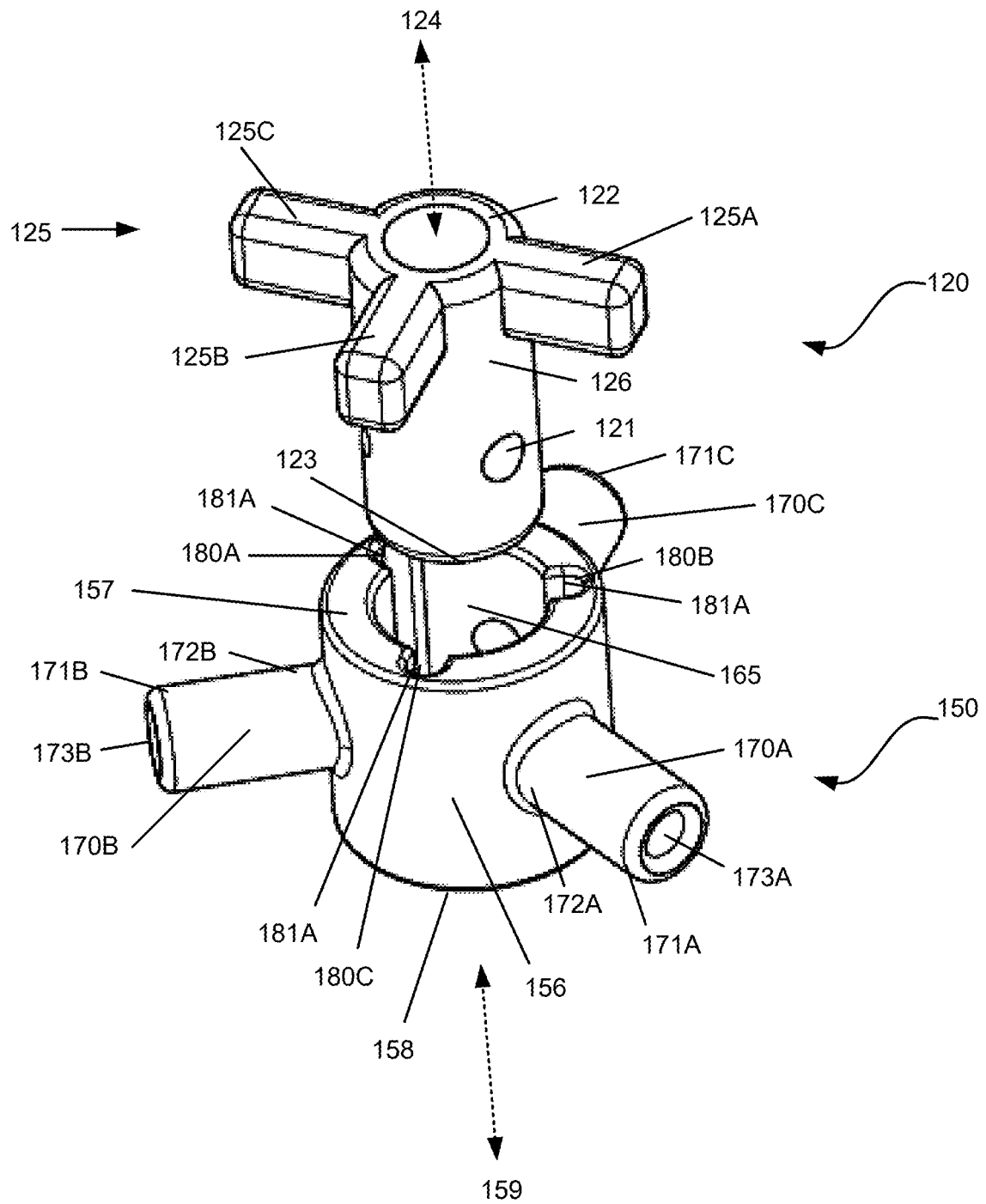
FIG. 5 shows a perspective view of an embodiment of a safety valve according to the second aspect of the invention.
Figure 6:
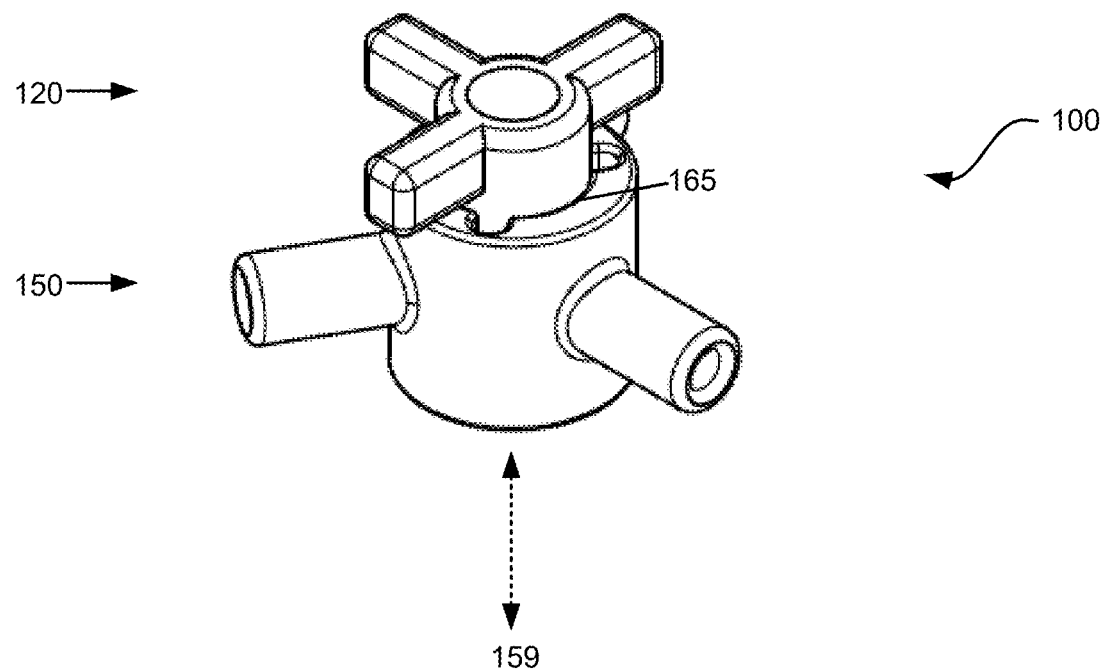
FIG. 6 shows a perspective view of the safety valve shown in FIG. 5 in an assembled configuration.
Figure 6:
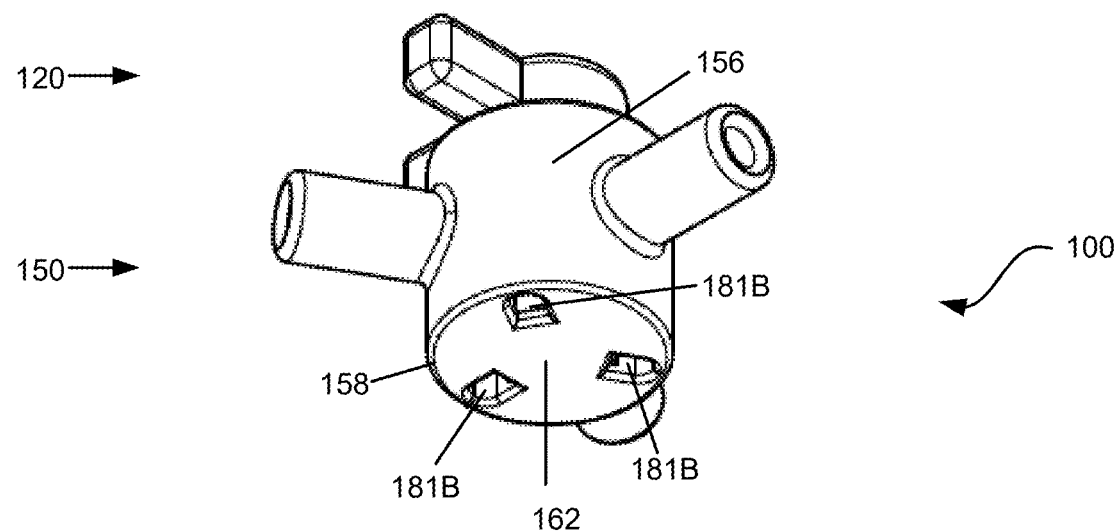

The regulating device 340 comprises a fifth 424 and a sixth 425 valve, the valves 424, 425 are valves as shown in FIG. 5-7. The valves 424, 425 are arranged on each side of the loop element 320. The fifth valve 424 is further connected to an injection means 420 and the sixth valve 425 is further connected to a patient line 520.

The fifth valve 424 is arranged in a first configuration of least two different configurations, so that the flow of saline solution of H215O passes through the fifth valve 424 and is guided into the loop, and the injection means 420 is closed off from the rest of system. If the fifth valve 424 was arranged in a second configuration, the saline solution of H215O would then not be able to pass the fifth valve 424, the fifth valve 424 opening a connection between the loop 320 and the injection means 420.

The sixth valve 425 is arranged in a first configuration of least two different configurations, so that the saline solution of H215O passes through the sixth valve 425 and is guided further into the conveying tube 301 and back into the reservoir 281. If the sixth valve 425 was arranged in a second configuration, the saline solution of H215O would be guided into the patient line 520 and the part of the conveying tube 301 transporting the saline solution of H215O back into the reservoir 281, would be closed off by the sixth valve 425.

A first radiation detector 240 is arranged adjacent to the loop element 320. The first radiation detector 240 comprises a first and a second detector unit (not shown), wherein said first and second detector units measures a first and a second radioactivity value of said saline solution of H215O present in the loop element 320.

If the first and second radioactivity values differ by more than 20%, preferably 15%, more preferred 10% from a user preset threshold level, the processing unit will prevent an injection from occurring.

When the fifth 424 and sixth 425 valves are arranged in the second configuration, the fifth valve 424, the sixth valve 425 and the loop element 320 establish a first bolus of said saline solution of H215O. The first bolus has a predefined volume and radioactivity concentration.

The injection means 420 comprise a fourth valve 4423 and a collecting element 422. The collecting element 422 is a medical syringe 422. The fourth valve 423 is a valve as shown in FIG. 5-8. The medical syringe 422 may be manually controlled and/or automatically controlled by the processing unit. A second saline feed 401 is connected to the fourth valve 423.

The fourth valve 423 is arranged in a first configuration of least two different configurations, so that a connection is open between the medical syringe 422 and the fifth valve 424. If the fourth valve 423 was arranged in a second configuration, a connection between the medical syringe 422 and the second saline feed 401 would be open.

When the fourth valve 423 is in a second configuration the medical syringe 422 can collect a predefined second bolus of saline from said second saline feed 401.

The patient line 520, which is connected to the sixth valve 425 is also connected to a bubble detector 522, a check valve 523, a second sterile filter 524 and a patient 521.

The bubble detector 522 detects if any undesired bubbles are present in the first and/or second bolus. In the unexpected event that a bubble is detected, the processing unit, which is connected to the bubble detector 522, stops the injection into the patient.

The check valve 523 is a one-way valve. The valve 523 ensures that the first and/or second bolus, which has passed the valve 523, cannot pass back into the system. Likewise any fluid from the patient 521 cannot cross the check valve 523 and pass back into the system.

The second sterile filter 524 removes any unwanted particulate and microbial impurities that may be remaining, thus ensuring that the first and/or second bolus is sterile before entering the patient 521.

A second radiation detector 440 arranged adjacent to the patient line measures an injection profile of said first bolus.

The patient 521 may be positioned in a scanner such as a Positron emission tomography (PET) scanner (not shown), wherein the distribution of the radioisotope in the patient 521 can be monitored before, during and after injection of the first bolus.

Figure 2:
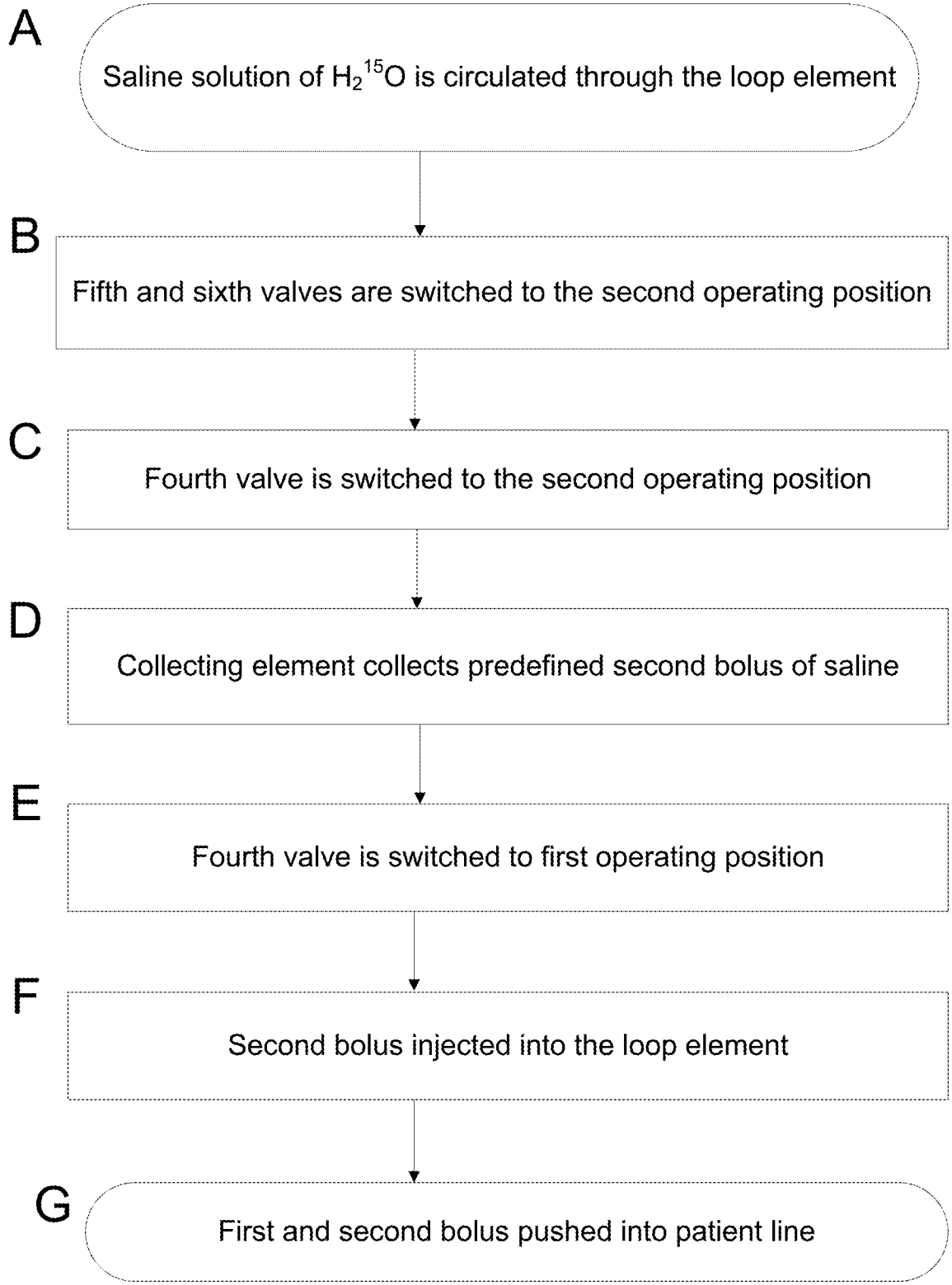
FIG. 2 is a flow chart illustrating the interaction between the bolus means and injecting means.

FIG. 2 is a flow chart illustrating the interaction of the bolus means and injecting means for providing an injectable saline solution of H215O having a predefined volume and radioactivity concentration.

In part A the second pump 302 connected to the conveying tube 301 regulates the flow of the saline solution of H215O, so that the saline solution of H215O is continuously pumped from the reservoir 281, through the conveying tube 301, the loop element 320 and the regulating device 340, thus providing readily available saline solution of H215O in the loop element 320 at any given time.

The regulating device 340 comprising the fifth and sixth valves 424, 425 arranged in the first configuration on each side of the loop element 320.

The first radiation detector 240 is arranged adjacent to the loop element 320. The first radiation detector 240 comprising the first and the second detector unit, which measures the first and the second radioactivity of said saline solution of H215O present in the loop element 320.

When the radioactivity in the loop element 320 reaches a desired level, which level may vary from measurement to measurement and from patient to patient, part B is initiated either automatically or manually.

In part B the fifth and sixth valves 424, 425 changes from the first configuration to a second configuration, so that the loop element 320 is not connected to the conveying tube 301 and the part of the system producing the saline solution of H215O. Further the patient 521 is also isolated from the rest of the system.

The fifth and sixth valves 424, 425 may change configuration simultaneously or individually. The second configuration of the fifth and sixth valves 424, 425 establishes the first bolus of said saline solution of H215O, the first bolus being the amount of said saline solution of H215O present in the loop element 320. The first bolus thus has a predefined volume and radioactivity concentration, which concentration is measured by the first and second detector units.

The loop element 320 has an adjustable volume that can be changed from patient to patient and from measurement to measurement.

In the second configuration the sixth valve 425 is connected to the patient line 520 and the fifth valve 424 is connected to the fourth valve 422.

In part C the fourth valve 423 is connected to the second saline feed 401 and the collecting element 422. When the fourth valve 423 is in the first configuration the connection is open between the collecting element 422 and the fifth valve 424.

The fourth valve 423 is switched to the second configuration, where the connection is then open between the collecting element 422 and the second saline feed 401.

In part D the collecting element 422 draws the desired amount of saline from the second saline feed 401, thus establishing the second bolus of saline. The second bolus of saline is preferably 5-150 ml, more preferred 10-100 ml.

In part E the fourth valve 423 is switched to the first configuration establishing a connection between the collecting element 422 comprising the second bolus of saline and the fifth valve 424.

In part F the fourth 423, fifth 424 and sixth 425 valves are arranged in the first configuration. The collecting element 422 injects the second bolus of saline into the loop element 320.

In part G the speed of the second bolus pushes both the first bolus of saline solution of H215O present in the loop element 320 and the second bolus itself into the patient line 520 and ultimately into the patient 521. The injection speed and amount of saline regulates the injection profile of the second bolus entering the patient 521.

The second radiation detector 440 adjacent to the patient line 520 measures the injection profile of said first bolus.

All the parts from A to G in the above description of FIG. 2 may be initiated and performed manually and/or automatically by the processing unit. The initiation of a part may also be dependent on the termination of another part.

FIG. 2 illustrates as an example one arrangement of the various parts. Part C and D wherein the second bolus of saline is established may also be performed before part B, wherein the first bolus of saline solution of H215O is established.

Figure 3A:
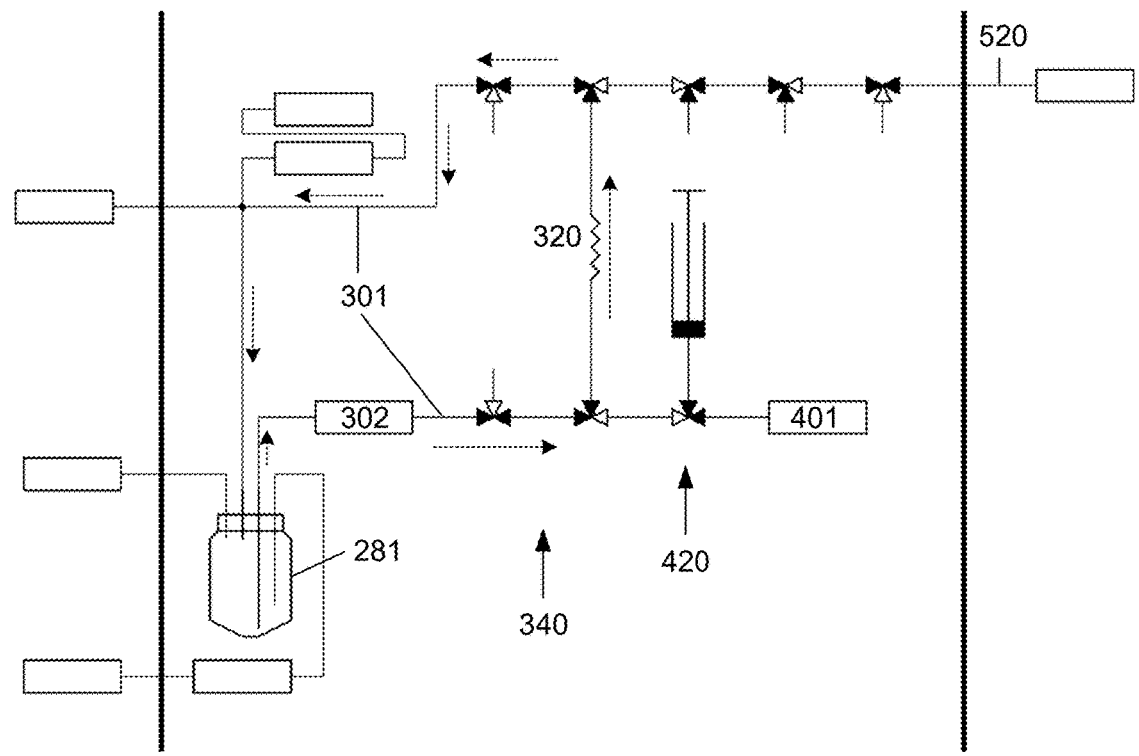
FIGS. 3A and 3B shows an embodiment and the first aspects according to the invention.
Figure 3B:
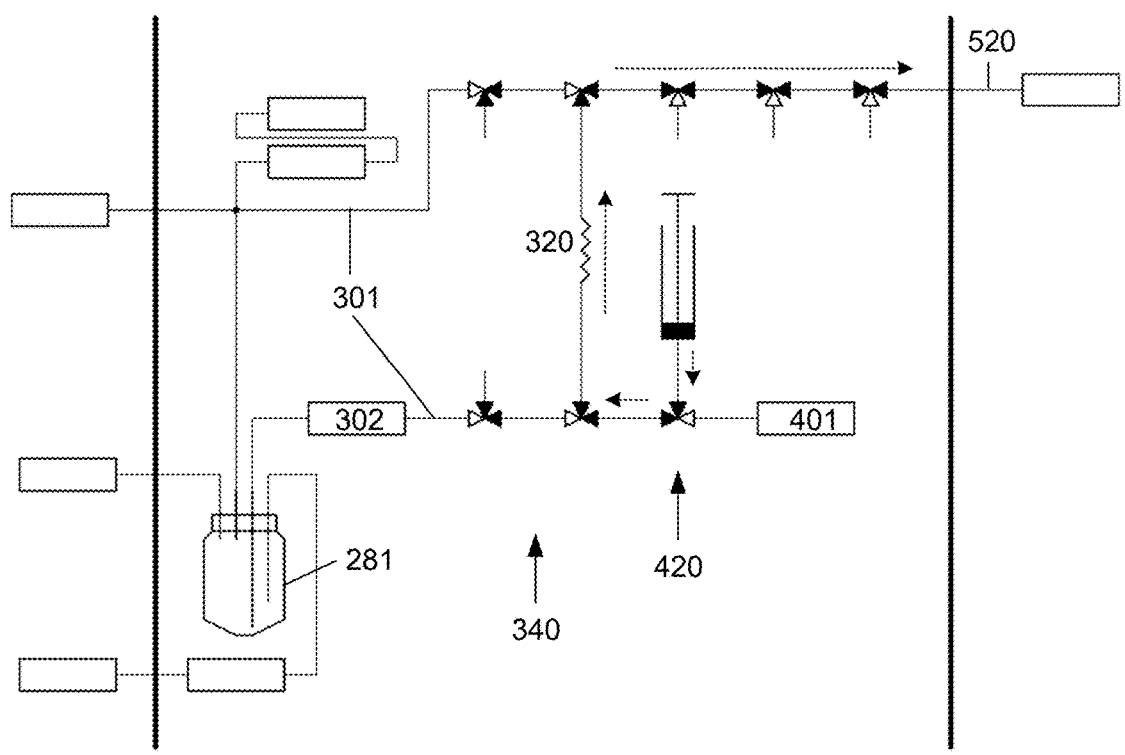

FIGS. 3A and 3B illustrates another embodiment of the first aspect according to the invention The reservoir 281 comprises a saline solution of H215O. The second pump 302 continuously pumps the saline solution of H215O from the reservoir 281 and into the conveying tube 301, through the regulating device 340 and the loop element 320 and back into the reservoir 281.

The regulating device 340 comprises a plurality of safety valves according to the third aspect of the invention. In FIGS. 3A and 3B the plurality of valves are represented as 7 valves.

In FIG. 3A the regulating device 340 is in the first configuration where the saline solution of H215O is pumped through the loop element 320. The injection means 420 is also in the first configuration where the second bolus of saline is established.

In FIG. 3B the regulation device 340 is in the second configuration, where the second bolus is established and the connection from the loop element 320 to the patient line 520 is open. The injection means 420 is also in the second configuration, where the second bolus of saline can be injected into the loop element 320 and the first and second bolus can enter the patient line 520.

Figure 4A:
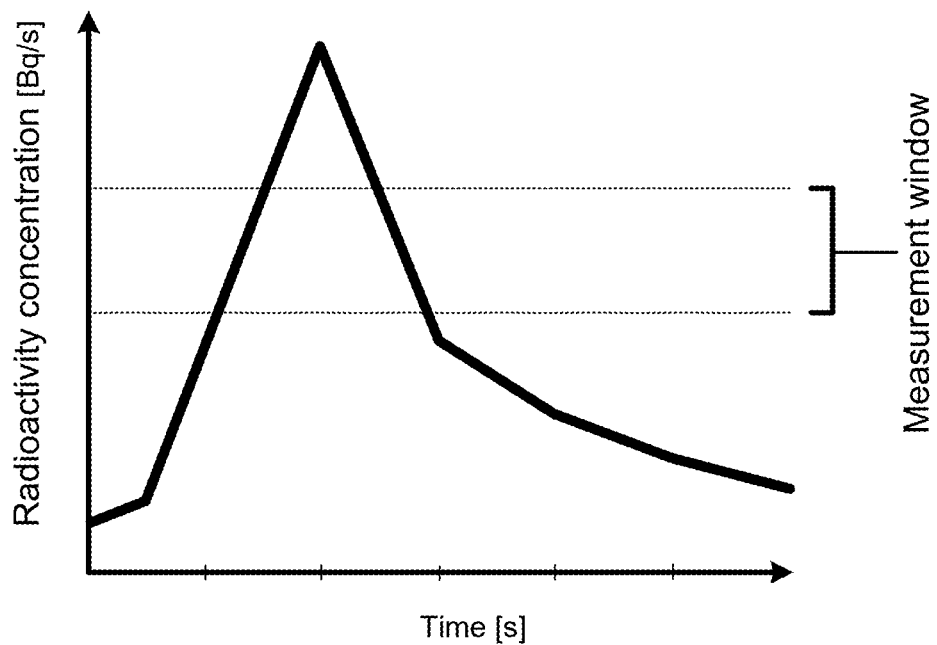
FIGS. 4A and 4B illustrates different injection profiles of the first bolus.

FIGS. 4A and B illustrates different injection profiles of the first bolus.

When regulating the injection profile of the first bolus, also referred to as bolus modulation, there are two external parameters that may utilized to influence the injection profile; injection speed and bolus volume.

According to the invention the volume of the first bolus is determined by the volume of the loop element 320. The volume of the loop element 320 may be altered depending on the bolus volume desired for the specific patient or measurement.

According to the invention the injection speed is determined by the injection means 420. The injection speed may be altered depending on the speed desired for the specific patient or measurement.

These parameters may be both manually and automatically altered.

Further the radioactivity is measured by the second radiation detector (not shown). Accurate measurements can only be done in a specific measurement window in which the radioactivity level is within a certain range. This range, and thus the measurement window may vary with different types of measurements performed.

Most commonly an injection is performed with a uniform injection speed, resulting in an injection profile as shown in FIG. 4A.

The uniform injection speed results in an injection profile with a sharp peak. The sharp peak limits the time period wherein the radioactivity level is inside the measurement window and thus the period wherein the second radiation detector can measure the radioactivity from the first injection profile.

Figure 4B:
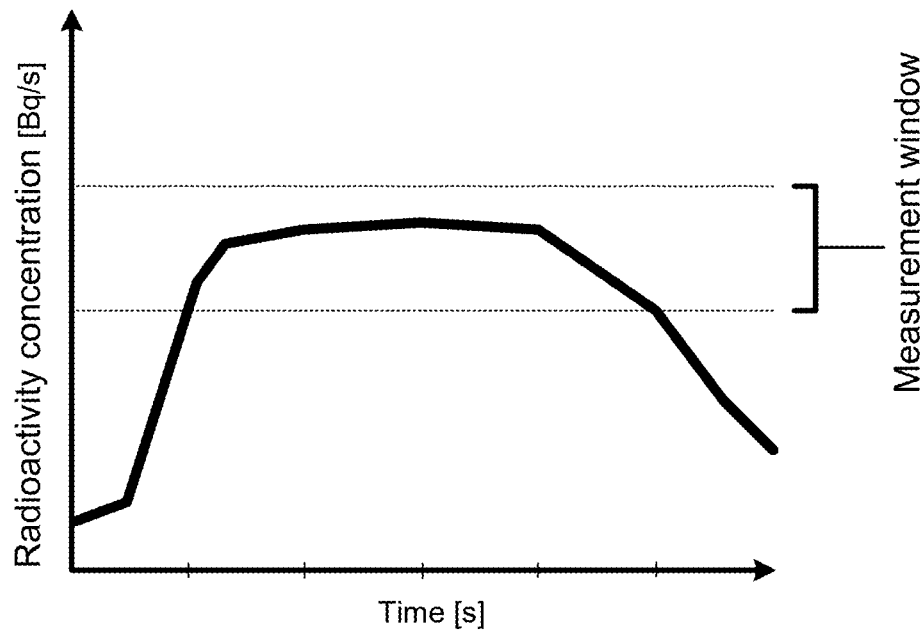

Conversely, if the injection is initiated at a slightly higher injection speed, which speed is then lowered during the injection, the injection profile as shown in FIG. 4B is more uniformly distributed in the region of interest, thus providing an injection profile where the radioactivity level is inside the measurement window for a longer period of time compared to the injection profile with an injection with uniform speed as shown in FIG. 4a.

With the radioactivity level being in the desired measurement window for a longer period it is for example possible to have a longer period of time in which the PET-scanner can accumulate data.

Further, the ability to modulate the injection profile is very useful during examinations in relation to cardiac studies, where the injection bolus may neither be too sharp nor too broad with respect to the patient's pulse. A too sharp profile will result in too few available data points in the available window. A too broad profile will result in that parameters necessary for the cardiac study, such as the distinct centroid time, cannot be determined.

In FIG. 5 a valve 100 is shown before assembly to an assembled valve 100. The valve comprises a valve element 120, a valve housing 150 and three overflow recesses 180A,B,C.

The valve element 120 comprises a first end 122 and a second end 123. The first and second ends 122, 123 define a first longitudinal axis 124. The valve element 120 is cylindrical. A flow channel 121 extends through the valve element 120 approximately perpendicular to the first longitudinal axis 124.

The valve housing 150 is cylindrical and comprises a cylindrical shell 156. The shell 156 comprises a first end 157, a second end 158 and a second longitudinal axis 159 extending between the first and the second end. The second longitudinal axis 159 is coaxial with the first longitudinal axis 124 of the valve element 120 when the valve is in the assembled configuration.

The valve housing 150 further comprises an internal spacing 165 enclosed by the shell 156 and a first, second and third valve opening 151A,B,C. Each valve opening 151A,B,C allows fluid flow into or out of the shell 156. The valve openings opening 151A,B,C are equally distributed with a mutual angle of approximately 120 degrees in a circumferential direction 160 of the shell.

The valve element 120 is axially movable along the second longitudinal axis 159, so that the second end and a part of the valve element 120 is insertable into the internal spacing 165 of the valve housing 150 to form the assembled valve 100.

The valve element 120 comprises a handle at the first end for rotating the valve element 120 inside the valve housing 150. The handle comprises a first, second and third protrusion 125A,B,C arranged in an outer circumference 126 of the valve element 120, the protrusions 125A,B,C extending radially from the valve element 120. The first and second protrusions 125A,B are arranged at an angle of 90 degrees with respect to each other. The second and third protrusions 125B,C are arranged at an angle of 90 degrees with respect to each other. The first and third protrusions 125A,C are arranged at an angle of 180 degrees with respect to each other. The protrusions 125A,B,C have a rectangular shape.

The valve housing 150 comprises a first, second and third hollow connection element 152A,B,C. The connection elements 152A,B,C each has a first end 153 A,B,C, a second end 154 A,B,C and an internal fluid space 155 A,B,C. The connection element 152 A,B,C are connected to the valve housing 150 at the second ends 154 A,B,C, so that said fluid spaces 155 A,B,C are in fluid contact with the three valve openings 151 A,B,C.

Three linear overflow recesses 180A,B,C are arranged in the valve housing 150, more specifically the overflow recesses 180A,B,C are arranged in the shell 156. Each overflow recesses 180A,B,C extends axially between said first and second ends 157, 158 of the shell 156. Each overflow recesses 180A,B,C has a first and a second outlet opening 181A,B. The overflow recesses 180A,B,C are equally distributed with a mutual angle of approximately 120 degrees in the circumferential direction 160 of the shell.

FIG. 6 shows a perspective view of the assembled valve 100.

The valve element 120 is arranged inside the internal spacing 165. The valve element 120 is rotatable inside the internal spacing 165 around the second longitudinal axis 159, so that the valve element 120 and valve housing 150 can change between at least three different open configurations 100A,B,C, the first, second and third open configurations are shown in FIGS. 7A, 7B and 7C.

The valve housing 150 comprises a circular bottom plate 162. The bottom plate 162 is connected to the second end 158 of the shell 156 extending over the entirety of the second end 158, so that the bottom plate 162 closes of the internal spacing 165 at said second end 158.

The three outlet openings 181B of the overflow recesses 180A,B,C are arranged in the bottom plate 162, so that excess fluid can be vented by the overflow recesses 180A, B,C through the bottom plate 162.

Figure 7A:
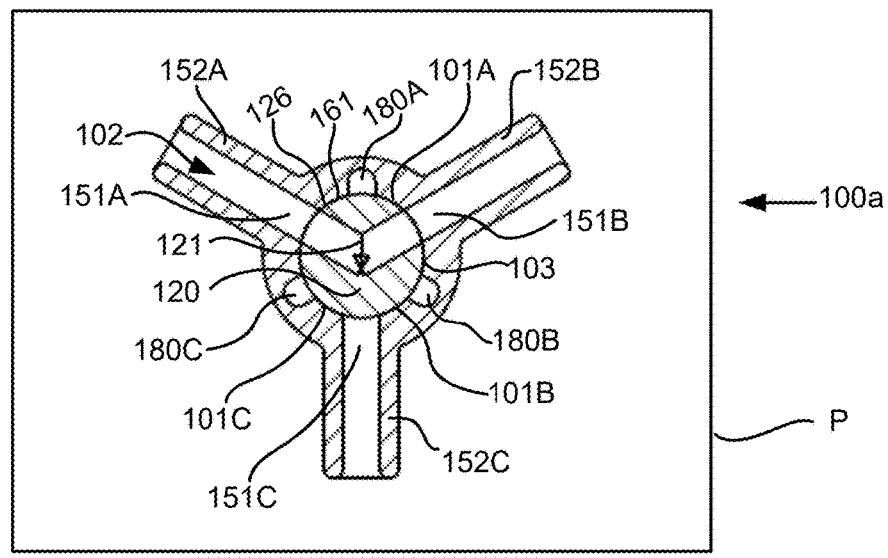
FIGS. 7A, 7B and 7C show a cross sectional views of the assembled safety valve in a first, second and third assembled configuration.
Figure 7B:
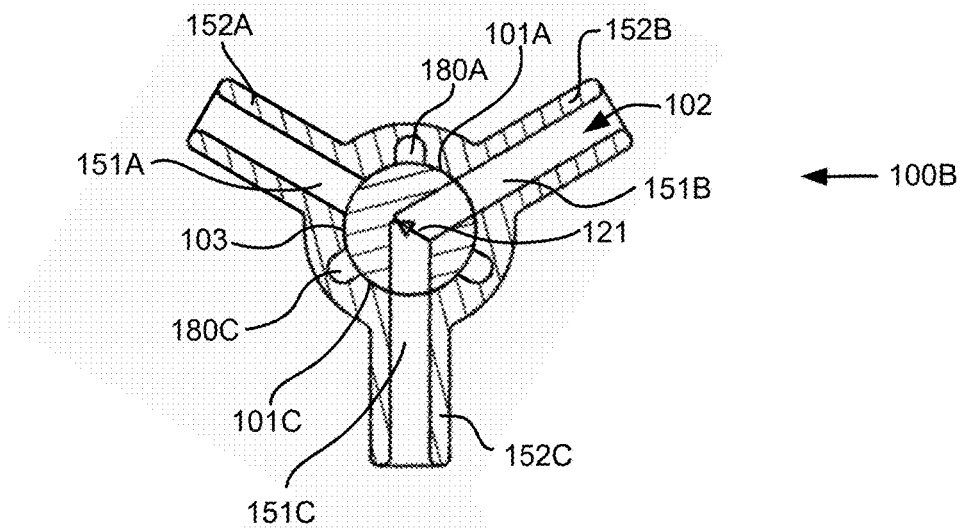
Figure 7C:
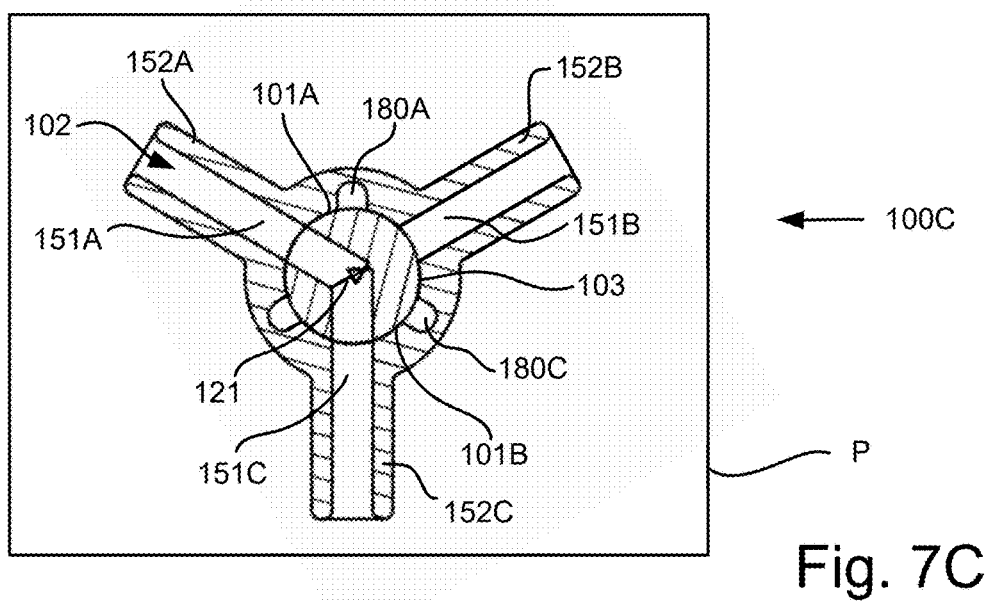

FIGS. 7A, 7B and 7C shows a cross sectional view of the assembled valve in a first, second and third assembled configuration.

In FIG. 7A-C a first, second and third connection element 152A,B,C is connected to the first, second and third valve openings 151A,B,C.

The valve element 120 and the valve housing are in contact with each other in three contact areas 101A,B,C. More specifically the outer circumference 126 of the valve element 120 is adjacent to an inner circumference 161 of the shell 156 of the valve housing 156 in the three contact areas 101A,B,C. Each of the contact areas 101A,B,C forms a fluid block 103.

Each overflow recess 180A,B,C is arranged between the valve element 120 and the valve housing 150. The overflow recesses 180A,B,C are not in fluid communication with the flow channel 121, The first overflow recess 180A is positioned to establish an interruption of the first contact area 101A. The second overflow recess 180B is positioned to establish an interruption of the second contact area 101B. The third overflow recess 180C is positioned to establish an interruption of the third contact area 101C.

Each overflow recess 180A,B,C establishes an interruption of said contact areas 101A,B,C, so that each overflow recess 180A,B,C establishes a safety relief vent that vents overflow fluid, which in case of overpressure passes through said fluid block 103, through said respective outlet openings 181A,B (not shown).

In FIG. 7A the assembled valve 100 is shown in a first assembled open configuration. The first and second valve openings 151A,B are connected by the flow channel 121. The third valve opening 151C is not connected to the flow channel 121.

The first assembled open configuration 100A has a flow path 102 through the first and second connection elements 152A,B, the flow channel 121 and the first and second valve openings 151A,B.

The second and third contact areas 101B,C each forms the fluid block 103 that prevents fluid flow into third valve opening 151C which is not connected to the flow channel 121. If any fluid passes the fluid block 103 in the second contact area 101B, the fluid will be vented through the second overflow recess 180B. If any fluid passes the fluid block 103 in the third contact area 101C, the fluid will be vented through the third overflow recess 180C.

In FIG. 7B the assembled valve 100 is shown in a second assembled open configuration. The second and third valve openings 151B,C are connected by the flow channel 121. The first valve opening 151A is not connected to the flow channel 121.

The second assembled open configuration 100B has a flow path 102 through the second and third connection elements 152B,C, the flow channel 121 and the second and third valve openings 151B,C.

The first and third contact areas 101A,B each forms the fluid blocks 103 that prevents fluid flow into first valve opening 151A which is not connected to the flow channel 121. If any fluid passes the first block 103 in the first contact area 101C, the fluid will be vented through the first overflow recess 180C. If any fluid passes the fluid block 103 in the second contact area 101B, the fluid will be vented through the second overflow recess 180B.

In FIG. 7C the assembled valve 100 is shown in a third assembled open configuration. The first and third valve openings 151A,C are connected by the flow channel 121. The second valve opening 151B is not connected to the flow channel 121.

The third assembled open configuration 100C has a flow path 102 through the first and third connection elements 152A,C, the flow channel 121 and the first and third valve openings 151A,C.

The first and second contact areas 101A,B each forms the fluid blocks 103 that prevents fluid flow into first valve opening 151A which is not connected to the flow channel 121. If any fluid passes the first block 103 in the first contact area 101C, the fluid will be vented through the first overflow recess 180C. If any fluid passes the fluid block 103 in the second contact area 101B, the fluid will be vented through the second overflow recess 180B.

In FIGS. 7A and 7C a plane P is illustrated. The valve openings 151A,B,C and the flow path 121 are arranged in the same plane P and extends in said plane P.

Figure 8:
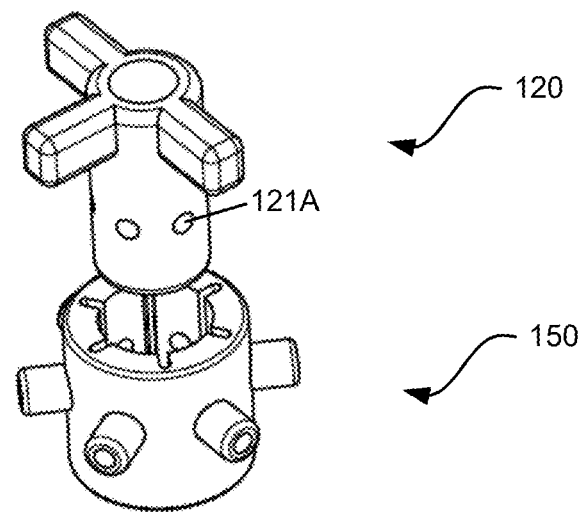
FIG. 8 shows a perspective view of an embodiment of the valve according to the third aspect of the invention.
Figure 9:
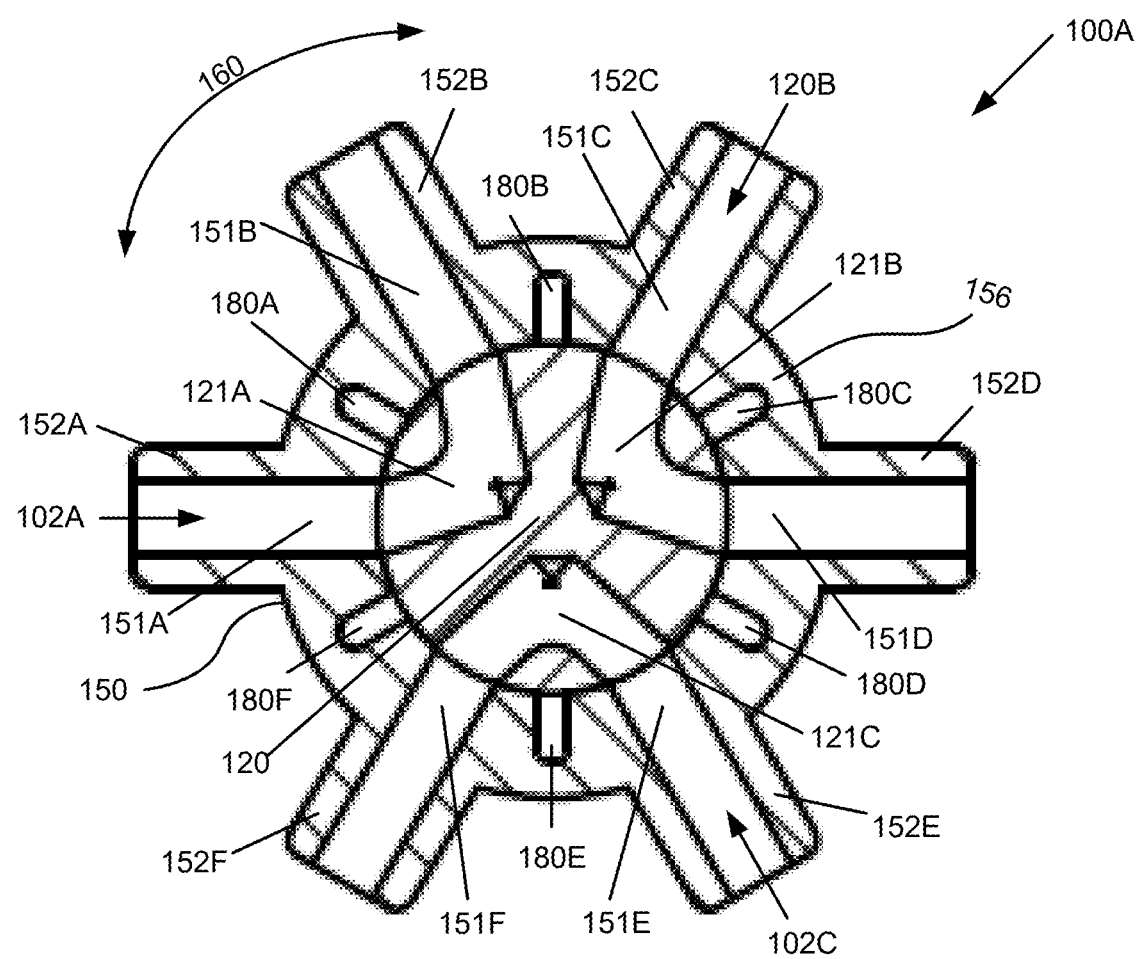
FIG. 9 shows a cross sectional views of the safety valve shown in FIG. 8 in an assembled position.

Said plane P is approximately perpendicular to the first and second axis 124, 159 (shown in FIG. 5) when the valve is in the assembled configuration In FIGS. 8 and 9 an embodiment of the safety valve according to the third aspect of the invention is shown in an unassembled position and an assembled position respectively. This embodiment is constructed corresponding to the embodiment shown in FIGS. 5-7 with the following differences:

The valve element 120 has three flow channels 121A,B,C, each flow channel extending through the valve element 120.

The valve housing 150 has six valve opening 151A,B,C,D,E,F. Each valve opening 151A,B,C,D,E,F allows fluid flow into or out of the shell 156. The valve openings opening 151A,B,C,D,E,F are equally distributed with a mutual angle of approximately 60 degrees in the circumferential direction 160 of the shell. The valve housing 150 has six hollow connection elements 152A,B,C,D,E,F.

The valve comprises six overflow recesses 180A,B,C,D,E,F. The overflow recesses are equally distributed with a mutual angle of approximately 60 degrees in the circumferential direction 160 of the shell.

The assembled valve 100 can change between six different open configurations 100A,B,C wherein in one open configuration three flow paths 102A,B,C are defined through the three flow channels 121A,B,C and three sets of said valve openings, and in another of said open configurations three different flow paths 102D,E,F through the three flow channels 121A,B,C and another, different three set of said valve openings, and in the third of said open configurations three different flow paths 102G,H,I through the three flow channels 121A,B,C and another, different three set of said valve openings.

The following items are embodiments of the invention:
1. A valve 100 for controlling a flow of $H_2{}^{15}O$ for use in Positron Emission Tomography, the valve 100 comprising:
   a valve element 120 with a flow channel 121 extending through the valve element 120,
   a valve housing 150 with at least three valve openings 151A,B,C, each valve opening 151A,B,C allowing fluid flow into or out of said valve 100, and
   at least two overflow recesses, each with at least one outlet opening,
   wherein the valve element 120 and valve housing 150 are connectable to form an assembled valve 100, the valve element 120 and the valve housing 150 being in contact with each other in a contact area,
   wherein the assembled valve 100 can be arranged in at least two, different configurations, one of said configurations defining a flow path through the flow channel 121 and one set of said valve openings, and another of said configurations defining a flow path through the flow channel 121 and another, different set of said valve openings, and
   wherein in each of said at least two configurations:
     each overflow recess is arranged between the valve element 120 and the valve housing 150,
     at least two of the valve openings are connected by the flow channel 121,
     at least one of the valve openings is not connected to the flow channel 121,
     said contact area forms a fluid block preventing fluid flow into said at least one valve opening not connected to the flow channel 121,
     the overflow recesses are not in fluid communication with the flow channel 121,
     each overflow recess is positioned to establish an interruption of said contact area so that the overflow recesses establish safety relief vents that vent overflow fluid, which in case of overpressure passes through said fluid block, through said respective outlet openings, so that in said at least two configurations said overflow fluid is prevented from entering into said at least one valve opening not connected to the flow channel 121.

2. A valve 100 according to item 1, wherein the valve housing 150 further comprises a connection element having a first and a second end and an internal fluid space, the connection element being connected to the valve housing 150 at the second end, so that said fluid space is in fluid contact with one of said at least three valve openings 151A,B,C.

3. A valve 100 according to item 1 or 2, wherein the at least two overflow recesses are arranged in the valve housing 150 and/or in the valve element 120.

4. A valve 100 according to any one of the preceding items wherein;
the valve element 120 further comprises a first end and a second end defining a first longitudinal axis, and
the valve housing 150 further comprises;
a shell comprising a first end and a second end and a second longitudinal axis extending between the first and the second end, the second longitudinal axis being coaxial with the first longitudinal axis,
an internal spacing for receiving the valve element 120, said internal spacing being enclosed by the shell, and
the at least three valve openings 151A,B,C being arranged in the shell each opening allowing fluid flow into or out of the internal spacing,
wherein the least two overflow recesses extends axially between said first and second ends of the shell,
wherein the valve element 120 is axially movable along the second longitudinal axis, so that a part of the valve element 120 is insertable into the internal spacing of the valve housing 150 to form the assembled configuration and the valve element 120 is rotatable inside the internal spacing around the second longitudinal axis, so that the valve element 120 and valve housing 150 can change between said least two different configurations,
wherein when the valve element 120 is arranged inside the internal spacing in said two different configurations, each overflow recess is arranged between the valve element 120 and the shell.

5. A valve 100 according to any one of the preceding items, wherein the valve housing 150 comprise three valve openings 151A,B,C and/or the valve comprise 3 overflow recesses and/or the valve element 120 comprise one flow channel 121.

6. A valve 100 according to any one of the preceding items, wherein the at least two overflow recesses are arranged in the shell and/or the at least two overflow recesses extends between and opens into the first and/or second ends of the shell and/or the at least two overflow recesses extends between and opens into the first and/or second ends of the valve element 120.

7. A valve 100 according to any one of the preceding items, wherein the shell is cylindrical and/or the valve element 120 is cylindrical and/or the valve openings are equally distributed around a circumference of the shell, the valve openings preferably being distributed with a mutual angle of approximately 120 degrees in a circumferential direction.

8. A system for preparing and injecting $H_2^{15}O$ for use in Positron Emission Tomography, said system comprising;
producing means for producing a saline solution of $H_2^{15}O$,
bolus means for establishing a first bolus for injection, said first bolus comprising said saline solution of $H_2^{15}O$ and having a predefined volume and radioactivity concentration, said bolus means comprising a valve 100, and
regulating means for regulating an injection profile of the first bolus.

9. A producing means for a system according to item 8, the producing means comprising;
a converting element for converting a gas mixture 221 comprising $^{15}O$ and $H_2$ to $H_2^{15}O$ under increased temperature,
a valve control element 250 for regulating a flow of said gas mixture 221,
a combining means for combining $H_2^{15}O$ with saline from a first saline feed to produce a saline solution of $H_2^{15}O$,
a first radiation detector 240 for measuring the radioactivity in said saline solution of $H_2^{15}O$,
wherein said valve control element 250 is regulated by the first radiation detector 240.

10. A producing means according to item 9, wherein the combining means comprise;
a reservoir 281 for receiving $H_2^{15}O$ and the first saline solution,
a second gas waste for venting any excess gas from said reservoir 281,
a third pump being connected at one end to the reservoir 281 and at another end to a decay line, the decay line being connected to a liquid waste,
wherein the third pump pumps excess liquid waste from the reservoir 281 through the decay line and into the liquid waste,
and/or the combining means further comprise;
a first pump connected to the first saline feed for providing the reservoir 281 with the saline solution, and
a pH-measuring device connected to the decay line,
wherein the first pump is regulated by the pH-measuring device.

11. A bolus means for a system according to item 8, wherein the bolus means comprise;
a reservoir 281 comprising a saline solution of $H_2^{15}O$,
a conveying tube 301 for circulating the saline solution of $H_2^{15}O$ from the reservoir 281 through a loop element 320 and a regulating device 340 and back into said reservoir 281,
a second pump 302 for regulating said flow,
wherein the regulating device 340 comprises a valve, the regulating device 340 having a first and a second configuration, where the second configuration of the regulating device 340 establishes a first bolus of said saline solution of $H_2^{15}O$, the first bolus having a predefined volume and radioactivity concentration.

12. A bolus means according to item 11, wherein the valve is a valve according to any one of items 1 to 5, and/or
the loop element 320 has an adjustable volume, and/or
a first radiation detector 240 is arranged adjacent to the loop element 320, the first radiation detector 240 comprising a first and a second detector unit, wherein said first and second detector units measures a first and a second radioactivity value of said saline solution of $H_2^{15}O$ present in the loop element 320.

13. A regulating means for a system according to item 8, the regulating means comprising;
a second saline feed 401,
a loop element 320 comprising a first bolus of said saline solution of $H_2^{15}O$,
an injection means 420 for collecting a predefined second bolus of saline from said second saline feed 401 and injecting said second bolus at a predefined speed into the loop element 320, so that the second bolus pushes the first bolus into a patient line 520, a second radiation detector 440 adjacent to the patient line 520, said radiation detector measuring an injection profile of said first bolus, wherein said injection speed and volume of the second bolus regulates the injection profile of the first bolus.

14. A method for preparing $H_2{}^{15}O$ for use in Positron Emission Tomography, said method comprising the steps of;

converting a gas mixture 221 comprising $^{15}O$ and $H_2$, to $H_2{}^{15}O$ under increased temperature, providing a valve control element 250 for regulating a flow of said gas mixture 221, combining $H_2{}^{15}O$ with saline from a first saline feed to produce a saline solution of $H_2{}^{15}O$, providing a first radiation detector 240 for measuring the radioactivity in said saline solution of $H_2{}^{15}O$, regulating said gas mixture 221 flow with the first radiation detector 240, providing a reservoir 281 for receiving the saline solution of $H_2{}^{15}O$, providing a second gas waste for venting any excess gas from said reservoir 281, providing a third pump, the third pump being connected at one end to the reservoir 281 and at another end to a decay line, the decay line being connected to a liquid waste, pumping with the third pump any excess liquid waste from the reservoir 281 through the decay line and into the liquid waste, providing a conveying tube 301 and a second pump 302 for circulating the saline solution of $H_2{}^{15}O$ from the reservoir 281 through a loop element 320 and back into said reservoir 281, providing a regulating device 340, establishing a first bolus of said saline solution of $H_2{}^{15}O$ in the loop element 320, the first bolus having a predefined volume and radioactivity concentration, providing a second saline feed 401, collecting a predefined second bolus of saline from said second saline feed 401, injecting said second bolus at a predefined speed into the loop element 320, so that the second bolus pushes the first bolus into a patient line 520, measuring with a second radiation detector 440 adjacent to the patient line 520 a injection profile of said first bolus, regulating the injection profile of the first bolus with said injection speed and volume of the second bolus.

15. A system according to item 8, wherein the valve is according to any one of item 1 to 7, and/or
the producing means is according to item 9 or 10 and/or
the bolus means is according to item 11 or 12 and/or
the regulating means is according to item 13 and/or
the valve is according to any one of item 1 to 7, and the producing means is according to item 9 or 10 and/or
the valve is according to any one of item 1 to 7, and the bolus means is according to item 11 or 12 and/or
the valve is according to any one of item 1 to 7, and the regulating means is according to item 13 and/or
the producing means is according to item 9 or 10, and the bolus means is according to item 11 or 12 and/or
the producing means is according to item 9 or 10, and the regulating means is according to item 13 and/or
the bolus means is according to item 11 or 12, and the regulating means is according to item 13 and/or
the valve is according to any one of item 1 to 7, and the producing means is according to item 9 or 10, and the bolus means is according to item 11 or 12 and/or
the valve is according to any one of item 1 to 7, and the producing means is according to item 9 or 10, and the regulating means is according to item 13 and/or
the valve is according to any one of item 1 to 7, and the bolus means is according to item 11 or 12, and the regulating means is according to item 13 and/or
the producing means is according to item 9 or 10, and the bolus means is according to item 11 or 12, and the regulating means is according to item 13 and/or
the valve is according to any one of item 1 to 7, and the producing means is according to item 9 or 10, and the bolus means is according to item 11 or 12, and the regulating means is according to item 13.

What is claimed is:

1. A method for preparing $H_2{}^{15}O$ for use in Positron Emission Tomography, said method comprising the steps of;

converting a gas mixture comprising $^{15}O$ and $H_2$, to $H_2{}^{15}O$ under increased temperature;

providing a valve control element for regulating a flow of said gas mixture;

combining $H_2{}^{15}O$ with saline from a first saline feed to produce a saline solution of $H_2{}^{15}O$;

providing a first radiation detector for measuring the radioactivity in said saline solution of $H_2{}^{15}O$;

regulating said gas mixture flow with the first radiation detector;

providing a reservoir for receiving the saline solution of $H_2{}^{15}O$;

providing a gas waste for venting any excess gas from said reservoir;

providing a first pump, the first pump being connected at one end to the reservoir and at another end to a decay line, the decay line being connected to a liquid waste;

pumping with the first pump any excess liquid waste from the reservoir through the decay line and into the liquid waste;

providing a conveying tube and a second pump for circulating the saline solution of $H_2{}^{15}O$ from the reservoir through a loop element and back into said reservoir;

providing a regulating device;

establishing a first bolus of said saline solution of $H_2{}^{15}O$ in the loop element, the first bolus having a predefined volume and radioactivity concentration;

providing a second saline feed;

collecting a predefined second bolus of saline in a collecting element from said second saline feed, the predefined second bolus having a predefined volume;

injecting said second bolus at a predefined speed into the loop element, so that the second bolus pushes an entire predefined volume of the first bolus from the loop element into a patient line, wherein the loop element is located upstream from and connected to the patient line such that the first bolus is pushed from the loop element directly into the patient line; and regulating an injection profile of the first bolus with said injection speed and volume of the second bolus.

* * * * *